US011241458B2

(12) United States Patent
Turzi et al.

(10) Patent No.: US 11,241,458 B2
(45) Date of Patent: *Feb. 8, 2022

(54) CELL PREPARATIONS FOR EXTEMPORANEOUS USE, USEFUL FOR HEALING AND REJUVENATION IN VIVO

(71) Applicant: RegenLab USA LLC, New York, NY (US)

(72) Inventors: Antoine Turzi, Mollens (CH); Donald Du Toit, Western Cape (ZA)

(73) Assignee: RegenLab USA LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/065,098

(22) Filed: Oct. 7, 2020

(65) Prior Publication Data

US 2021/0030805 A1 Feb. 4, 2021

Related U.S. Application Data

(63) Continuation of application No. 16/793,296, filed on Feb. 18, 2020, which is a continuation of application
(Continued)

(30) Foreign Application Priority Data

Aug. 21, 2006 (WO) .................. PCT/EP2006/065493

(51) Int. Cl.
| | |
|---|---|
| *A61K 35/19* | (2015.01) |
| *A61K 35/15* | (2015.01) |
| *A61K 35/18* | (2015.01) |
| *A61K 35/36* | (2015.01) |
| *A61Q 19/00* | (2006.01) |
| *A61K 8/98* | (2006.01) |
| *A61L 24/00* | (2006.01) |
| *A61L 24/10* | (2006.01) |
| *A61L 26/00* | (2006.01) |
| *A61M 1/36* | (2006.01) |
| *A61K 35/14* | (2015.01) |
| *A61K 35/16* | (2015.01) |
| *A61K 38/36* | (2006.01) |
| *A61K 35/28* | (2015.01) |
| *A61K 35/30* | (2015.01) |
| *A61K 35/32* | (2015.01) |
| *A61K 35/34* | (2015.01) |
| *A61K 35/35* | (2015.01) |
| *A61K 35/38* | (2015.01) |
| *A61K 35/39* | (2015.01) |
| *A61K 35/51* | (2015.01) |
| *A61K 38/48* | (2006.01) |
| *A61L 27/36* | (2006.01) |
| *A61L 27/38* | (2006.01) |
| *A61Q 19/08* | (2006.01) |

(52) U.S. Cl.
CPC .............. *A61K 35/19* (2013.01); *A61K 8/981* (2013.01); *A61K 8/983* (2013.01); *A61K 35/14* (2013.01); *A61K 35/15* (2013.01); *A61K 35/16* (2013.01); *A61K 35/18* (2013.01); *A61K 35/28* (2013.01); *A61K 35/30* (2013.01); *A61K 35/32* (2013.01); *A61K 35/34* (2013.01); *A61K 35/35* (2013.01); *A61K 35/36* (2013.01); *A61K 35/38* (2013.01); *A61K 35/39* (2013.01); *A61K 35/51* (2013.01); *A61K 38/363* (2013.01); *A61K 38/4833* (2013.01); *A61L 24/0005* (2013.01); *A61L 24/106* (2013.01); *A61L 26/0042* (2013.01); *A61L 26/0057* (2013.01); *A61L 27/3691* (2013.01); *A61L 27/3886* (2013.01); *A61M 1/3693* (2013.01); *A61Q 19/00* (2013.01); *A61Q 19/08* (2013.01); *A61K 2300/00* (2013.01); *A61K 2800/87* (2013.01); *A61L 2430/02* (2013.01); *A61M 2202/0427* (2013.01); *C12Y 304/21005* (2013.01)

(58) Field of Classification Search
CPC ............................... A61Q 19/00; A61K 8/983
See application file for complete search history.

(56) References Cited

U.S. PATENT DOCUMENTS

| | | | |
|---|---|---|---|
| 3,852,194 | A | 12/1974 | Zine, Jr. |
| 4,101,422 | A | 7/1978 | Lamont et al. |
| 4,148,764 | A | 4/1979 | Lamont et al. |
| 4,190,535 | A | 2/1980 | Luderer et al. |
| 4,350,593 | A | 9/1982 | Kessler |
| 4,814,418 | A | 4/1989 | Saunders |
| 5,053,134 | A | 10/1991 | Luderer et al. |

(Continued)

FOREIGN PATENT DOCUMENTS

| | | |
|---|---|---|
| CA | 2181462 | 6/1996 |
| CA | 2181462 C | 8/2002 |

(Continued)

OTHER PUBLICATIONS

Respondents' Responses to Complainant's RegenLab USA LLC's High Priority Objections Nos. 1-2, *In the Matter of Certain Blood Separation and Cell Preparation Devices*, Inv. No. 337-TA-1147 (Nov. 1, 2019).

(Continued)

*Primary Examiner* — Paul J Holland
(74) *Attorney, Agent, or Firm* — Pillsbury Winthrop Shaw Pittman, LLP

(57) ABSTRACT

The present invention relates to new plasma or new platelet-rich plasma preparations, new cell dissociation methods, new cell associations or compositions, a method of preparation thereof, a use thereof, devices for the preparation thereof and preparations containing such a platelet-rich plasma preparation and cell associations or compositions. Specifically, the invention provides plasma or platelet-rich plasma alone or in cell composition preparations for use in tissue regeneration and bone regeneration and pain reduction.

32 Claims, 4 Drawing Sheets

Related U.S. Application Data

No. 16/103,453, filed on Aug. 14, 2018, now Pat. No. 10,881,691, which is a continuation of application No. 15/605,696, filed on May 25, 2017, now Pat. No. 10,052,349, which is a continuation of application No. 15/044,498, filed on Feb. 16, 2016, now Pat. No. 10,092,598, which is a continuation of application No. 14/021,196, filed on Sep. 9, 2013, now abandoned, which is a continuation of application No. 12/438,236, filed as application No. PCT/EP2007/058695 on Aug. 21, 2007, now Pat. No. 8,529,957.

(56) References Cited

U.S. PATENT DOCUMENTS

| | | | |
|---|---|---|---|
| 5,236,604 | A | 8/1993 | Fiehler |
| 5,494,590 | A | 2/1996 | Smith et al. |
| 5,510,237 | A | 4/1996 | Isogawa et al. |
| 5,667,963 | A | 9/1997 | Smith et al. |
| 5,733,545 | A | 3/1998 | Hood, III |
| 5,906,744 | A | 5/1999 | Carroll et al. |
| 5,977,056 | A | 11/1999 | Powell-Jones et al. |
| 6,428,527 | B1 | 8/2002 | Jones et al. |
| 6,472,162 | B1 | 10/2002 | Coelho et al. |
| 6,979,307 | B2 | 12/2005 | Beretta et al. |
| 9,962,480 | B2 | 5/2018 | Esteron |
| 2002/0123140 | A1 | 9/2002 | Bandyopadhyay et al. |
| 2002/0187130 | A1 | 12/2002 | Kindness et al. |
| 2004/0059255 | A1 | 3/2004 | Manoussakis et al. |
| 2004/0071786 | A1 | 4/2004 | Grippi et al. |
| 2004/0151709 | A1 | 8/2004 | Gorrochategui Barrueta et al. |
| 2005/0170327 | A1 | 8/2005 | Sumida et al. |
| 2006/0128016 | A1 | 6/2006 | Tokushima et al. |
| 2009/0186341 | A1 | 7/2009 | Dahm |
| 2010/0015229 | A1 | 1/2010 | Turzi et al. |

FOREIGN PATENT DOCUMENTS

| | | |
|---|---|---|
| WO | 03/092894 | 11/2003 |
| WO | 2003/092894 A3 | 11/2003 |
| WO | 2006/136870 | 12/2006 |
| WO | 2008/022651 | 2/2008 |
| WO | 2008/022651 A1 | 2/2008 |
| WO | 2008/023026 | 2/2008 |
| WO | 2011/110948 | 9/2011 |

OTHER PUBLICATIONS

Complainant's RegenLab USA LLC's Prehearing Brief, *In the Matter of Certain Blood Separation and Cell Preparation Devices*, Inv. No. 337-TA-1147 (Oct. 29, 2019).
Respondents' Response to Complainant's Motion to Terminate the Investigation Based on Withdrawal of the Complaint, *In the Matter of Certain Blood Separation and Cell Preparation Devices*, Inv. No. 337-TA-1147 (Nov. 15, 2019).
Reply Memorandum in Support of Respondents' Motion for an Order to Show Cause Why RegenLab and it Previous Counsel Should Not be Sanctioned, *In the Matter of Certain Blood Separation and Cell Preparation Devices*, Inv. No. 337-TA-1147 (Dec. 2, 2019).
RegenLab, A-CP Tube Evaluation on 60 Volunteers Cells Counts & Functionality Performance, RL-A-CP PERF-V4 (Oct. 24, 2017).
RegenLab, Summary of cellular composition of PRP prepared with RegenLab devices (2019).
Eclipse PRP Instructions for Use, PRPIFU Rev. 6.
Tropocells PRP Analysis (Redacted).
Estar Medical, "Tropocells PRP Simplicity for Success".
Evacuated Tube with Polyester Gel + Sodium Citrate Solution (General Supply Agreement REGEN00017499-17519, at 17516) (Becton Dickinson).
Estar_ITC1147_021226, U.S. Trademark Registration for "VACUTAINER" (Oct. 29, 1946).
Estar_ITC1147_010888, BD Vacutainer® Evacuated Blood Collection System (2004).
Estar_ITC1147_010913, BD Vacutainer® Tube Guide (Dec. 2005).
Vacutainer RegenTHT® Estar_ITC1147_016151-016167 (RegenLab SA).
Estar_ITC1147_020177, Cascade Autologous Platelet SystemBrochure (2005).
Winkelman et al., "How RBCs Move Through Thixotropic Gels", Specimen Processing, Laboratory Medicine, vol. 30, Issue 7, published Jul. 1999, pp. 476-477, 2 pgs.
"Autologous PRP" RegenLab, May 2, 2006, pp. 1-2. https://web.archive.org/web/20060502171522/hllp:/lwww.regenkil.com/products.html.
"BD Vacutainer CPT—Cell Preparation Tube with Sodium Citrate, Beckton, Dickinson and Co.", (2003), pp. 1-14.
"BD Vacutainer Tube Guide", Beckton, Dickinson and Co., published 2006, pp. 1-8. http://www.bd.com/resource.aspx?IDX=11068.
"Effect of Platelet Rich Plasma and Keratinocyte Suspensions on Wound Healing", ClinicalTrials.gov, pp. 1-19 https://clinicaltrials.gov/cl2/show/NCT00856934, 2009.
"Regen Lab: Products for Tissue Repair", Regan Lab, Apr. 2006, pp. 1-2. hllps://web-beta.archive.org/web/20060426121922://http://www.regenkit.com/.
"RegenPRP-Kit Medical Device lla CE1250", RegenLab Geneve, Sep. 26, 2004, pp. 1-17 https://web.archive.org/web/20050313100219/http://lwww.regenkil.com/docs/RegenPRP-Kit_ang.pdf.
2003 Swiss Assoc. for Quality and Management Systems, IQNet certificate, Risk analysis, contract, pp. 1-34.
Charles F. Arkin et al: "Tubes and Additivies for Venous Blood Specimen Collection; Approved Standard-Fifth Edition", NCCLS document H1-A5, 940 West Valley Road, Suite 1400, Wayne, Pennsylvania 19087-1898 USA; 2003, ,vol. 23, No. 33, pp. 1-31. SBN 1-56238-519-4.
Claim Chart for U.S. Appl. No. 12/438,236, attached with letter dated Jul. 30, 2012 from Marshall J_ Schmitt at Michael Best & Friedrich LLP, pp. 1-38.
De Oliveira & Saldanha. "An overview about erythrocyte membrane". Clinical Hemorheology and Microcirculation, Institute of Molecular Medicine, Libson, Portugal, published 2010, vol. 44, pp. 63-74.
Ju Toit Of, et al.: "Soll and hard-tissue augmentation with platelet-rich plasma: Tissue culture dynamics, egeneration and molecular biology perspective", International Journal of Shoulder Surgery, published 2007, vol. 1, pp. 64-73. http://www.internationalshoulderjournal.org/article.asp?issn=0973-6042;year=2007;volume=1;issue=2;spage=64; page=73;aulast=du&utm source=realself.com&utm medium=referral.
Everts et al.: "Platelet rich plasma and platelet gel, A review.", Journal of Extra-Corporeal Technology, Orlando FL, USA, published May 18, 2006, vol. 38, pp. 174-187.
Fulton, J_ "Breast Contouring with 'Gelled' Autologous Fat: A 10-Year Update" International Journal of Cosmetic Surgery and Aesthetic Dermatology, 2003, pp. 155-163, vol. 5, No. 2.
Gadol et al.: "A new method for separating mononuclear cell from whole blood" Diagnostic Immunology, published 1985, vol. 3, Issue No. 3, pp. 145-154 https://www.ncbi.nlm.nih.gov/pubmed/3931958.
Garratty, Telen & Petz: "Red Cell Antigens as Functional Molecules and Obstacles to Transfusion, Part I. Erythrocyte Blood Group Antigens: Physiologic and Pathologic Functions of Red Cell Antigen-Bearing Molecules", by Marilyn J_ Teien. Hematology American Society of Hematology Education Program, published: 2002, pp. 445-462.
Graziani et al.: "The in vitro effect of different PRP concentrations on osteoblasts and fibroblasts.", Clinical Oral Implants Research, published Apr. 2006, vol. 17, issue No. 2, pp. 212-219.
J.R. Storry: "Review: the function of blood group-specific RBC membrane components", Immunohematology Journal of Blood Group Serology and Education, published 2004, vol. No. 20, issue No. 4, pp. 206-216.

Laurens, I.: "Development of a new extraction method for platelet-rich plasma and partial purification of platelet-derived growth factor and transforming growth factor beta". Dissertation submitted in fulfillment of the requirements for he degree Magister Scientiae in the Dept. of Pharmacology, Faculty of Health Sciences, Univ. of Pretoria, South Africa., published Oct. 2013, pp. 1-148.

Letter dated Jul. 30, 2012 from Marshall J_ Schmitt at Michael Best & Friedrich LLP, pp. 1-2.

Parkinson, E. K. et al. "3. The Epidermis" Culture of Epithelial Cells, 2002, pp. 65-94, nd 2 Edition.

Perttila, J_ et al.: "Plasma Fibronectin concentrations in blood products.", Intensive Care Med., published Jan. 1990, vol. 16, issue No. 1, pp. 41-43; ISSN 1432-1238, https://doi.org/10.1007/BF01706323.

Raffoul, et al.: "Impact of platelets concentrate and keratinocyte suspension on wound healing—a prospective randomized trial", The International Journal of Artificial Organs, published 2008, pp. 1-16.

Regen Lab brochure entitled RegenPRP-Kil available at www.regenkit.com as of May 2, 2006. Copy obtained from archived version of May 2, 2006 on the Wayback Machine, pp. 1-17 http://web.archive.org/web/20060502171406/ http://www.regenkil.com:80/doc/RegenPRP-Kit_english.pdf.

Regen Lab Brochure, "RegenPRP-KIT", available at www.regenkit.com as of Sep. 26, 2004, pp. 1-18.

Regen Lab Presentation, "Innovation in Biological Tissue Regeneration", 2005, pp. 1-54.

Regen Lab Webpage available at www.regenkil.com, as of May 2, 2006 https://web.archive.org/web/20060502171344/hllp://regenkit.com:80/company.html.

Regen Lab webpage available at www.regenkil.com as of May 16, 2006 https://web.archive.org/web/20060516102752 http://www.regenkit.com:80/regen_ THT.html.

Regen-Kit Instructions for Use, May 2, 2006, pp. 1-2. nttps://web.archive.org/web/20060502171707 /http:/www.regenkil.com/doc/RegenPRP-Kit-IFU .pdf.

RegenLab Certification from Swiss Association for Quality and Management Systems (SQS) for the developing and marketing of medical devices, Feb. 21, 2005, and Regen Lab CE Certification "X( 1250" for the Regen Kit under Registration No. 2378801, from SQS, Dec. 23, 2003, 2 pages. https://web.archive.org/web/20060511153104/http:/lwww.regenkit.com:80/doc/ReGen%20Lab%20%20ISO%209001%20&%2013485.pdf.

Research Study, Comparison of EmCyte GS30-PurePRP® II, EmCyte GS60-PurePRP® II, Arteriocyte MAGELLAN, Stryker REGENKIT® THT, and ECLIPSE PRP. Principle Investigator Robert Mandie, PhD, Biosciences Research Associates, Cambridge, MA, May 2016, pp. 1-14.

Rheinwald, J. et al. "Serial Cultivation of Strains of Human Epidermal Keratinocytes: the Formation of Keratinizing :Colonies from Single Cells" Cell, Nov. 1975, pp. 331-344, vol. 6.

Rheinwald, J. G. et al. "Formation of a Keratinizing Epithelium in Culture by a Cloned Cell Line Derived from a Teratoma" Cell, Nov. 1975, pp. 317-330, vol. 6.

Ronfard, V. et al. "Use of human keratinocytes cultured on fibrin glue in the treatment of burn wounds" Burns, 1991, pp. 181-184, vol. 17, No. 3.

Slighter et al.: "Platelet Transfusion Therapy", Chapter 14 in "Platelets In Hematologic and Cardiovascular Disorders". Edited by Paolo Gresele et al.; Cambridge University Press, Cambridge United Kingdom, 2008, pp. 242-260.

The Merck Manual for Health Care Professionals, "Appendix II Normal Laboratory Values", 2011, pp. 1-9.

Translation Swiss 2003 Assoc. and Management Systems, IQNet certificate, Risk analysis, contract, pp. 23-24.

Tsay et al.: "Differential growth factor retention by platelet-rich plasma composites", Journal of Oral and Maxillofacial Surgery, vol. No. 63, Issue No. 4, 2005, pp. 521-528, ISSN 0278-2391, http://www.sciencedirect.com/science/article/pii/S0278239104016349.

Tull, S. P. et al. "Cellular Pathology of Atherosclerosis Smooth Muscle Cells Promote I\Adhesion of Platelets to Cocultured Endothelial Cells" Gire. Res., 2006, pp. 98-104, vol. 98.

U.S. Office Action U.S. Appl. No. 15/044,498 dated Feb. 5, 2018, 13 pages.

U.S. Office Action U.S. Appl. No. 15/605,696 dated Jun. 15, 2017, 7 pages.

U.S. Office Action U.S. Appl. No. 15/065,696 dated Dec. 26, 2017, 18 pages.

U.S. Office Action U.S. Appl. No. 15/605,696 dated Jul. 17, 2017, 19 pages.

Van Laethem et al.: "Diagnosis of human immunodeficiency virus infection by a polymerase chain assay evaluated in patents harboring strains of diverse geographical origin" Journal of Virological Methods, published Feb. 1998, vol. 70, issue 2, pp. 153-166 Department of Microbiology & Immunology, Rega Institute for Medical Research and University Hospitals, Leuven, Belgium.

Arkin, C.F., Tubes and Additives for Venous Blood Specimen Collection; Approved Standard Fifth Edition, CLSI, vol. 23, No. 33 (2003).

Arsoumanian, L., Tech Talk, vol. 4, No. 2 (Nov. 2005).

Gadol, N., A New Method for Separating Mononuclear Cells From Whole Blood, Diagnostic Immunology 3:145-154 (1985).

Marx, R.E., Platelet-Rich Plasma: Evidence to Support Its Use, J. Oral Maxillofac. Surg., 62:489-496 (Apr. 2004).

Mazzucco, L., Platelet-rich plasma and platelet gel preparation using Plateltex®, Vox Sanguinis (2008) DOI: 10.1111/j.1423-0410.2008.01027.x (Jan. 7, 2008).

Raffoul, W., et al., Impact of platelets concentrate and keratinocyte suspension on wound healing—a prospective randomized trial. *The International Journal of Artificial Organs*, Jul. 2008. Uploaded to ResearchGate by author on Oct. 14, 2014.

Kevy, Set. Al., Comparison of Methods for Point of Case Preparation of Autologous Platelet Gel. The Journal of The American Society of Extra-Corporeal Technology, vol. 36, 2004.

Commission Investigative Staff's Notice of Prior Art, *In the Matter of Certain Blood Separation and Cell Preparation Devices*, Inv. No. 337-TA-1147 (Jul. 23, 2019).

Declaration of Christopher J. Stankus in Support of Complainant's Opposition to Motion to Compel, *In the Matter of Certain Blood Separation and Cell Preparation Devices*, Inv. No. 337-TA-1147 (Aug. 12, 2019).

Complainant RegenLab USA LLC's Live Witness Outlines, *In the Matter of Certain Blood Separation and Cell Preparation Devices*, Inv. No. 337-TA-1147 (Sep. 27, 2019).

Respondents' Outlines of Live Direct Testimony, *In the Matter of Certain Blood Separation and Cell Preparation Devices*, Inv. No. 337-TA-1147 (Sep. 27, 2019).

Commission Investigative Staff's Ground Rule 9.3.2. Outline, *In the Matter of Certain Blood Separation and Cell Preparation Devices*, Inv. No. 337-TA-1147 (Oct. 3, 2019).

Complainant RegenLab USA LLC's Rebuttal Witness Outlines, *In the Matter of Certain Blood Separation and Cell Preparation Devices*, Inv. No. 337-TA-1147 (Oct. 11, 2019).

Respondents' Outlines of Live Rebuttal Testimony, *In the Matter of Certain Blood Separation and Cell Preparation Devices*, Inv. No. 337-TA-1147 (Oct. 11, 2019).

Respondents' Pre-hearing Statement, *In the Matter of Certain Blood Separation and Cell Preparation Devices*, Inv. No. 337-TA-1147 (Oct. 29, 2019).

Respondents' Pre-hearing Brief, *In the Matter of Certain Blood Separation and Cell Preparation Devices*, Inv. No. 337-TA-1147 (Oct. 29, 2019).

Respondents' Response to Commission Investigative Staff's High Priority Objection No. 2, *In the Matter of Certain Blood Separation and Cell Preparation Devices*, Inv. No. 337-TA-1147 (Nov. 1, 2019).

ISO 10989-33, Biological evaluation of medical devices—Part 3: Tests for genotoxicity, carcinogenicity and reproductive toxicity (2d. ed. Oct. 15, 2003).

ISO 1099311, Biological evaluation of medical devices—Part 11: Tests for systemic toxicity (2d ed. Aug. 15, 2006).

ISO 10993-12, Biological evaluation of medical devices—Part 12: Sample preparation and reference materials (4th ed. Jul. 1, 2012).

Order Denying Respondents' Motion for Partial Summary Determination of Non-Infringement, *In the Matter of Certain Blood Separation and Cell Preparation Devices*, Inv. No. 337-TA-1147 (Sep. 19, 2019).
RegenLab, Regen BCT—Evaluation on 60 Volunteers Cells Counts & Functionality Performance (RL-BCT PERF-V6 Oct. 24, 2017).
*Regen Lab SA v. Estar Mdical LTD*, Patent Court Decision, 2019 R.P.C. 7 (Jan. 2019).
RegenLab, RegenTHT, Evaluation on 60 Volunteers Cells Counts & Functionality Performance (RL-THT PERF-V4 Oct. 24, 2017).
RegenPRP-Kit Brochure (RegenLab Geneve), 2004.
Estar_ITC1147_017319, BD VacutainerTM CPTTM Cell Preparation Tube with Sodium Citrate (Jan. 2003).
Estar_ITC1147_017319, BD Vacutainer Plus Plastic Blood Collection Tubes (Feb. 2003).
Estar_ITC1147_012738, Regen PRP-Kit Medical Device lla CE 1250. Copy obtained from archived version of Mar. 13, 2005 on Wayback Machine (Mar. 13, 2005).
Estar_ITC1147_012763, Regen Lab presentation entitled "Innovation in Biological Tissue Regeneration", 2005. Copy obtained from archived version of May 14, 2005 on Wayback Machine (May 14, 2005).
Perttilä, J., et al., Plasma Fibronectin concentrations in blood products. *Intensive Care Med*. 1990; 16(1): 41-3.
Tsay et al., Differential growth factor retention by platelet-rich plasma composites. *J. Oral. Maxillofac. Surg*. 2005. 63: 521-528.
Ex. SMX0004 to Commission Investigative Staff's Claim Construction Brief, *In the Matter of Certain Blood Separation and Cell Preparation Devices*, Inv. No. 337-TA-1147 (Jun. 19, 2019)—Houghton, V., "A new spin: Examining the theory behind the use of platelet rich plasma for dermatologic procedures," Dermatology World (2018), 28(5):50-56.
Ex. SMX0005 to Commission Investigative Staff's Claim Construction Brief, *In the Matter of Certain Blood Separation and Cell Preparation Devices*, Inv. No. 337-TA-1147 (Jun. 19, 2019)—Final Rejection Office Action (Jul. 5, 2017), file history of U.S. Appl. No. 15/369,966.
Ex. SMX0006 to Commission Investigative Staff's Claim Construction Brief, *In the Matter of Certain Blood Separation and Cell Preparation Devices*, Inv. No. 337-TA-1147 (Jun. 19, 2019)—Response After Final Action (Sep. 1, 2017), file history of U.S. Appl. No. 15/369,966.
Ex. SMX0007 to Commission Investigative Staff's Claim Construction Brief, *In the Matter of Certain Blood Separation and Cell Preparation Devices*, Inv. No. 337-TA-1147 (Jun. 19, 2019)—Arkin, Charles F., et al., "Tubes and Additives for Venous Blood Specimen Collection; Approved Standard-Fifth Edition," National Committee for Clinical Laboratory Standards (NCCLS), document HI-A5, 2003, vol. 23, No. 33, pp. 1-31.
Ex. SMX0008 to Commission Investigative Staff's Claim Construction Brief, *In the Matter of Certain Blood Separation and Cell Preparation Devices*, Inv. No. 337-TA-1147 (Jun. 19, 2019)—Shorter Oxford English Dictionary, 6th Ed. (2007) (excerpts).
Ex. SMX0009 to Commission Investigative Staff's Claim Construction Brief, *In the Matter of Certain Blood Separation and Cell Preparation Devices*, Inv. No. 337-TA-1147 (Jun. 19, 2019)—Notice of Allowance (Jun. 27, 2018), file history of '894 Patent.
Ex. SMX0010 to Commission Investigative Staff's Claim Construction Brief, *In the Matter of Certain Blood Separation and Cell Preparation Devices*, Inv. No. 337-TA-1147 (Jun. 19, 2019)—McGraw-Hill Dictionary of Chemistry, 2nd ed. (2003) (excerpts).
Ex. SMX0011 to Commission Investigative Staff's Claim Construction Brief, *In the Matter of Certain Blood Separation and Cell Preparation Devices*, Inv. No. 337-TA-1147 (Jun. 19, 2019)—Gadol, Nancy, et al., "A New Method for Separating Mononuclear Cells From Whole Blood," Diagnostic Immunology (1985), vol. 3, Issue No. 3, pp. 145-154.
Ex. SMX0012 to Commission Investigative Staff's Claim Construction Brief, *In the Matter of Certain Blood Separation and Cell Preparation Devices*, Inv. No. 337-TA-1147 (Jun. 19, 2019)—Declaration of Andrea Pigni (filed Sep. 1, 2017), file history of U.S. Appl. No. 15/369,966.
Ex. SMX0013 to Commission Investigative Staff's Claim Construction Brief, *In the Matter of Certain Blood Separation and Cell Preparation Devices*, Inv. No. 337-TA-1147 (Jun. 19, 2019)—U.S. Pat. No. 3,852,194 to Zine.
Ex. SMX0014 to Commission Investigative Staff's Claim Construction Brief, *In the Matter of Certain Blood Separation and Cell Preparation Devices*, Inv. No. 337-TA-1147 (Jun. 19, 2019)—U.S. Pat. No. 5,667,963 to Smith, et al.
Ex. SMX0015 to Commission Investigative Staff's Claim Construction Brief, *In the Matter of Certain Blood Separation and Cell Preparation Devices*, Inv. No. 337-TA-1147 (Jun. 19, 2019)—McGraw-Hill Dictionary of Scientific and Technical Terms, 5th ed. (1994) (excerpts).
Notice of Institution, *In the Matter of Certain Blood Separation and Cell Preparation Devices*, Inv. No. 337-TA-1147 (Mar. 6, 2019).
Notice, 84 Fed. Reg. 88914 (Mar. 12, 2019).
Complainant's Unopposed Motion for Partial Termination of this Investigation with Respect to Certain Asserted Patent Claims, *In the Matter of Certain Blood Separation and Cell Preparation Devices*, Inv. No. 337-TA-1147 (Jun. 3, 2019).
Respondents' Initial Markman Brief, *In the Matter of Certain Blood Separation and Cell Preparation Devices*, Inv. No. 337-TA-1147 (Jun. 14, 2019).
Respondents' Rebuttal Markman Brief, *In the Matter of Certain Blood Separation and Cell Preparation Devices*, Inv. No. 337-TA-1147 (Jun. 28, 2019).
Notice of Commission Determination Not to Review an Initial Determination Terminating the Investigation with Respect to Certain Asserted Claims, *In the Matter of Certain Blood Separation and Cell Preparation Devices*, Inv. No. 337-TA-1147 (Jul. 1, 2019).
Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019).
Ex. 1 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—U.S. Pat. No. 10,064,894.
Ex. 2 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—Jul. 5, 2017 Office Action, U.S. Appl. No. 15/369,966.
Ex. 3 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—Sep. 1, 2017 Response to Final Office Action, U.S. Appl. No. 15/369,966.
Ex. 4 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—U.S. Pat. No. 9,833,478.
Ex. 5 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—Originally Filed Claims, U.S. Appl. No. 15/797,016.
Ex. 6 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—Dec. 26, 2017 Office Action, U.S. Appl. No. 15/797,016.
Ex. 7 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—Examiner's Amendment to the Claims in U.S. Appl. No. 15/797,016.
Ex. 8 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—"Eclipse PRP: Infringement Claim Chart U.S. Pat. No. 10,064,894".

Ex. 9 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—"MyCells 510(k) Section 4: Device Description".

Ex. 18 to Respondents' Motion for Summary Determination of Non-Infringement of U.S. Pat. No. 10,064,894, *In the Matter of Certain Blood Separation and Cell Preparation Devices*, Inv. No. 337-TA-1147 (Jun. 27, 2019)—Charles F. Arkin et al., "Tubes and Additives for Venous Blood Specimen Collection: Approved Standard—Fifth Edition", NCCLS document H1-A5.

Transcript of Markman Hearing, *In the Matter of Certain Blood Separation and Cell Preparation Devices*, Inv. No. 337-TA-1147 (Jul. 18, 2019).

Reply Memorandum in Support of Respondents' Motion for Summary Determination of Non-Infringement, *In the Matter of Certain Blood Separation and Cell Preparation Devices*, Inv. No. 337-TA-1147 (Jul. 11, 2019).

Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019).

Ex. 1 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '894 Patent, Application (excerpts).

Ex. 2 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '894 Patent, Non-Final Rejection Office Action (dated Dec. 26, 2017).

Ex. 3 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '894 Patent, Examiner-Initiated Interview Summary (Jun. 27, 2018).

Ex. 4 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '894 Patent, Notice of Allowance (dated Jun. 27, 2019).

Ex. 5 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '966, Application (excerpts).

Ex. 6 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '966, Final Rejection Office Action (dated Jul. 5, 2017).

Ex. 7 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '966, Response After Final Office Action (dated Sep. 1, 2017).

Ex. 8 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—File History of the '966, Notice of Allowance (dated Sep. 29, 2017).

Ex. 9 to Commission Investigative Staff's Response to Respondents' Motion for Summary Determination of Non-Infringement of U.S. Pat. No. 10,064,894, *In the Matter of Certain Blood Separation and Cell Preparation Devices*, Inv. No. 337-TA-1147 (Jul. 8, 2019)—Complainant's Responses to Staff's First Set of Interrogatories, at Interrogatory No. 28 (Jun. 27, 2019).

Transcript of Tutorial, *In the Matter of Certain Blood Separation and Cell Preparation Devices*, Inv. No. 337-TA-1147 (Jul. 18, 2019).

Complainant's Opposition to Respondents' Motion for Summary Determination of Non-Infringement, *In the Matter of Certain Blood Separation and Cell Preparation Devices*, Inv. No. 337-TA-1147 (Jul. 8, 2019).

Complainant's Notice of Prior Art, *In the Matter of Certain Blood Separation and Cell Preparation Devices*, Inv. No. 337-TA-1147 (Jul. 23, 2019).

Respondents' Notice of Prior Art, *In the Matter of Certain Blood Separation and Cell Preparation Devices*, Inv. No. 337-TA-1147 (Jul. 23, 2019).

First Amended Complaint, *In the Matter of Certain Blood Separation and Cell Preparation Devices*, Inv. No. 337-TA-3361 (Feb. 15, 2019) 40 pgs.

Redacted Supplemental Decl. of Antoine Turzi, *In the Matter of Certain Blood Separation and Cell Preparation Devices*, Inv. No. 337-TA-3361 (Feb. 15, 2019) 15 pgs.

Letter to Sec. Barton from S. Ball re Confidential Treatment of Certain Exhibits Submitted with Amended Complaint, *In the Matter of Certain Blood Separation and Cell Preparation Devices*, Inv. No. 337-TA-3361 (Feb. 15, 2019) 2 pgs.

Complainant's Opening Claim Construction Brief, *In the Matter of Certain Blood Separation and Cell Preparation Devices*, Inv. No. 337-TA-1147 (Jun. 14, 2019) 22 pgs.

Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019) 3 pgs.

Decl. of Jeffrey J. Chalmers, Ph.D. In Support of Complainant's Opening Claim Construction Brief, *In the Matter of Certain Blood Separation and Cell Preparation Devices*, Inv. No. 337-TA-1147 (Jun. 14, 2019) 38 pgs.

Ex. A to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—U.S. Pat. No. 10,064,894, 27 pgs.

Ex. B to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Regenlab RegenKit—BCT Plus Instructions for Models RegenKit—BCT-1 Plus and RegenKit—BCT-2 Plus (May 2015) 7 pgs.

Ex. C to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Complainant's Responses and Objections to Respondents' First Set of Interrogatories (Nos. 1-50), *In the Matter of Certain Blood Separation and Cell Preparation Devices*, Inv. No. 337-TA-1147 (Mar. 25, 2019) 9 pgs.

Ex. D to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Additive, Oxford American Dictionary and Thesaurus (Am. Ed. 2003) 13 pgs.

Ex. E to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Complainant's Responses and Objections to Respondents' First Set of Requests for Admissions (Nos. 1-23), *In the Matter of Certain Blood Separation and Cell Preparation Devices*, Inv. No. 337-TA-1147 (Jun. 3, 2019) 5 pgs.

Ex. F to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Commission Investigative Staff's Proposed Claim Constructions, *In the Matter of Certain Blood Separation and Cell Preparation Devices*, Inv. No. 337-TA-1147 (May 31, 2019) 8 pgs.

Ex. G to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—U.S. Pat. No. 9,962,480, 17 pgs.
Ex. H to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Respondents' Initial Identification of Claim Terms for Construction (by letter), *In the Matter of Certain Blood Separation and Cell Preparation Devices*, Inv. No. 337-TA-1147 (May 21, 2019) 3 pgs.
Ex. J to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Letter from D. Melman to S. Ball re: Complaint, Identification of Claim Terms for Construction (by letter), *In the Matter of Certain Blood Separation and Cell Preparation Devices*, Inv. No. 337-TA-1147 (May 9, 2019).
Ex. K to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—instructions for Useof Eclipse PRP PPT-I Platelet Preparation System.
Ex. L to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Photographs of Eclipse PRP PPT-I Platelet Preparation Tube label and product.
Ex. M to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—U.S. Pat. No. 9,833,478.
Ex. N to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Letter from S. Ball to Counsel for Respondents (Apr. 3, 2019).
Ex. O to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Response to Final Office Action, U.S. Appl. No. 15/369,966 (dated Sep. 1, 2017).
Ex. P. to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—*Routine Hematology Procedures*, Excerpt from Textbook of Hematology (2d. ed. 1996).
Ex. Q to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Instructions for Use of Estar's Tropcells Platelet Rich Plasma Preparation System.
Redacted Complainant's Opposition to Respondents' Motion for Summary Determination of Non-Infringement, *In the Matter of Certain Blood Separation and Cell Preparation Devices*, Inv. No. 337-TA-1147 (Jul. 16, 2019).
Declaration of Andreas Pigni In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019).
Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019).
Declaration of Jeffrey J. Chalmers In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019).
Ex. A to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—U.S. Pat. No. 10,064,894.
Ex. B to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Declaration of Jeffrey J. Chalmers, Ph.D. in Support of Complainant's Opening Claim Construction Brief (Jun. 14, 2019).
Ex. C to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Declaration of Jeffrey J. Chalmers, Ph.D. in Support of Complainant's Rebuttal Claim Construction Brief (Jun. 28, 2019).
Ex. D to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Response to Office Action, U.S. Appl. No. 15/369,966 (dated Sep. 1, 2017).
Ex. E to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Declaration of Gary D. Fletcher in Support of Respondents' Opening Claim Construction Brief (Jun. 14, 2019).
Ex. F to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Instructions for use of the Eclipse PRP, PPT-I Platelet, Preparation System.
Ex. G to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Instructions for use of Estar Technologies Ltd.'s ("Estar") Platelet Rich Plasma Preparation System.
Ex. H to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Photographs of the Eclipse PRP Platelet Preparation Tube (PPT-I) product.
Ex. I to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Tech Talk (vol. 4, No. 2 Nov. 2005).
Ex. J to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—BD Life Sciences—Preanalytical Systems Product Catalog.
Ex. K to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Excerpts from the following dictionaries for the definition of "ingredient": a screenshot from the website https://www.dictionary.com/browse/ingredient (Jun. 28, 2019); The Merriam-Webster Dictionary (2004); Oxford American Dictionary and Thesaurus, American Edition (2003).
Ex. L to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—United States Patent Application Publication No. 2004/0071786.

Ex. M to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Respondent Estar Technologies Ltd.'s Supplemental Responses to Complainant's Interrogatories Nos. 6,14,15, 42, and 56.

Ex. P to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Excerpts of Complainant's First Set of Requests for Production of Documents and Things (Nos. 1-41) to Estar.

Ex. Q to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Excerpts of Respondent Estar Technologies Ltd. Responses and Objections to Complainant's First Set of Requests for Production of Documents and Things (Nos. 1-41).

Ex. R to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Discovery Committee Report for Apr. 2019, served on May 10, 2019.

Ex. S to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Discovery Committee Report for May 2019, served on Jun. 10, 2019.

Ex. T to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Correspondence exchanged between counsel for Complainant and Respondents.

Ex. W to Declaration of Christopher J. Stankus In Support of Complainant's Opposition to Respondents' Motion for Summary Determination of Non-Infringement, *In the Matter of Certain Blood Separation and Cell Preparation Devices*, Inv. No. 337-TA-1147 (Jul. 8, 2019)—Respondent Estar Technologies Ltd.'s Responses and Objections to Complainant's Fourth Set of Interrogatories (Nos. 16-24).

Complainant's Rebuttal Claim Construction Brief, *In the Matter of Certain Blood Separation and Cell Preparation Devices*, Inv. No. 337-TA-1147 (Jun. 28, 2019).

Declaration of Christopher J. Stankus In Support of Complainant's Rebuttal Claim Construction Brief, *In the Matter of Certain Blood Separation and Cell Preparation Devices*, Inv. No. 337-TA-1147 (Jun. 28, 2019).

Declaration of Jeffrey J. Chalmers, Ph.D. In Support of Complainant's Rebuttal Claim Construction Brief, *In the Matter of Certain Blood Separation and Cell Preparation Devices*, Inv. No. 337-TA-1147 (Jun. 28, 2019).

Ex. A to Declaration of Christopher J. Stankus In Support of Complainant's Rebuttal Claim Construction Brief, *In the Matter of Certain Blood Separation and Cell Preparation Devices*, Inv. No. 337-TA-1147 (Jun. 28, 2019)—Excerpt of MyCells 510(k) Report, Sections 4 and 5.

Ex. I to Decl. of Christopher J. Stankus In Support of Complainant's Opening Claim Construction Brief, *In the Matter of Certain Blood Separation and Cell Preparation Devices*, Inv. No. 337-TA-1147 (Jun. 14, 2019)—Commission Investigative Staff's Initial Identification of Claim Terms for Construction, *In the Matter of Certain Blood Separation and Cell Preparation Devices*, Inv. No. 337-TA-1147 (May 21, 2019).

CELL PREPARATIONS FOR EXTEMPORANEOUS USE, USEFUL FOR HEALING AND REJUVENATION IN VIVO

CROSS-REFERENCE TO RELATED APPLICATIONS

This application is a Continuation of U.S. Ser. No. 16/793,296, filed Feb. 18, 2020, which is a Continuation of U.S. Ser. No. 16/103,453, filed Aug. 14, 2018, which is a Continuation of U.S. Ser. No. 15/605,696, filed May 25, 2017, now U.S. Pat. No. 10,052,349, which is a Continuation of U.S. Ser. No. 15/044,498, filed Feb. 16, 2016, now U.S. Pat. No. 10,092,598, which is a Continuation of U.S. Ser. No. 14/021,196, filed Sep. 9, 2013, now abandoned, which is a Continuation of U.S. Ser. No. 12/438,236, filed Feb. 20, 2009, now U.S. Pat. No. 8,529,957, which is the U.S. national phase application of International Patent Application No. PCT/EP2007/058695, filed Aug. 21, 2007, which claims priority to PCT/EP2006/065493, filed Aug. 21, 2006, the disclosures of each of which are hereby incorporated by reference in their entirely, including all figures, tables and amino acid or nucleic acid sequences.

TECHNICAL FIELD

The present invention is related to the field of tissue regeneration, especially skin, cartilage, muscle, tendon, adipose tissue, cornea, peripheral nerves, spine and bone regeneration. It concerns more particularly new cell preparations as a biological scaffold, a method of preparation thereof, a use thereof, a device for the preparation thereof and preparations containing such cell preparation for extemporaneous use.

BACKGROUND

The importance of biological autologous materials in the healing process has been well documented. Most importantly, two biological autologous materials have been shown to be directly implicated in the formation of the structure of blood clots, which provide a haemostatic barrier whose role is to ensure hemostasis and seal the wound: (1) fibrin, which derives from the separation of plasma fibrinogen into two strands through the action of thrombin, and (2) the activated membranes of platelets.

The wound healing process is generally presented as the succession of a coagulation phase, an inflammatory process and a regeneration process.

The coagulation phase (blood clotting or clot formation) is a complex process whereby a damaged blood vessel wall is covered by a fibrin clot to stop hemorrhage and the repair of the damaged vessel is initiated by the release in large quantities of cytokines and growth factors from platelet alpha granules. The formation of blood clots (formed in physiological conditions by fibrin, platelets and red blood cells, among other blood components) is a natural phenomenon that results from tissue trauma and its role in the wound healing process, as well as in the union of bone fractures, is well-known.

The inflammation process, which follows the formation of a blood clot, is stimulated by numerous vasoactive mediators and chemotactic factors (specific signals in the form of proteins) released by white blood cells and platelets. These signals attract macrophages that "clean" the site from bacteria and foreign particles as well as red blood cells before the migration of new cells.

The tissue regeneration phase involves the chemoattraction and the mitosis of the undifferentiated cells in the scaffold (or growth matrix) formed by the blood clot. The new cells which multiply under the stimulation of platelet growth factors will replace damaged or destroyed cells injured by macrophages.

Growth factors and numerous plasma proteins, also called signaling molecules, which promote cell migration and division within blood clots, play a crucial role in the wound healing process.

Theoretically, it is possible to amplify the effects of these first phases in the wound-healing cascade by discarding the red blood cells and increasing the concentration of growth factors.

Blood clotting amplification can be defined as the formation of an "enriched clot (EC)". ECs are obtained through the use of platelet concentrates and have been described in *Platelets and Megacaryocytes* 2004, *vol* 1 & 2, *as "Structure and signals"*, Ed. Gibbins and Mahaut-Smith, Humana Press, N.J.

Platelet-rich plasma (PRP) can be defined as an autologous concentrate of platelets in a small volume of plasma; it has been developed as an autologous biomaterial and has proven to be useful in the heating and regeneration of tissues (Marx et al., 2004, *J. Oral Maxillofac. Surg.*, 62, 489-496). PRP not only consists in a platelet concentrate but also contains growth factors (such as platelet-derived growth factor: PDGF, vascular endothelial growth factor: VEGF, transforming growth factor: TGF and epidermal growth factor: EGF) that are actively secreted by platelets and are known to have a fundamental role in wound healing initiation process.

For example, PDGF is known to initiate connective tissue healing, including bone regeneration and repair. PDGF also increases mitogenesis (healing cells), angiogenesis (endothelial mitosis into functioning capillaries) and macrophage activation. VEGF released by the leukocytes is also known to have potent angiogenic, mitogenic and vascular permeability-enhancing activities on endothelial cells. TGF-$\beta$ promotes cell mitosis and differentiation for connective tissue and bone, acts on mesenchymal stem cells, preosteoblasts and fibroblasts and inhibits osteoclast formation. EGF is known to induce epithelial development and promote angiogenesis.

Platelet concentrates are generally used in dental implantology and bone surgery, notably in the USA. Various techniques of preparation of PRP by centrifugation processes have been developed. However, due to the sensitivity of the platelet cells and the variability of the efficiency of the methods of separation of the platelets from the red blood cells, a great variability exist among the methods used for the preparation of platelet concentrates (Marx et al., 2004, above; Roukis et al., *Adv. Ther.*, 2006, 23(2):218-37): for example, the laboratory material for in vitro diagnostic which is used for platelet preparation, leads to a poor platelet and other plasma components yield (Marx et al., 2004, above: Anitua 35%, Landsberg 30%, Clinaseal 39%, ACE surgical 33%, Curasan 29%). The automated settings from Biomet PCCS & GPS (Marx et al., 2004, above), which not only present the drawback of being a complex process with prohibitive costs for the process of a blood sample, lead to only a yield of 61% and SmatPreP from Harvest Technology 62%. In those systems, there is obviously an important loss of valuable biologic tissue from the patients, therefore there is the need for the development of a reliable process collecting the plasma cells with high yields, easy to use and cost effective.

It has been recently demonstrated that the positive effects of platelet-rich plasma on bone regeneration spans a limited range of platelet concentration and revealed that: an inhibitory effect occurs in the presence of more than $10^6$ platelets per µl, which is 3 to 4 times baseline counts (Weibrich et al., 2004, *Bone*, 34(4):665-71).

In addition, the obtaining of platelet concentrates still needs the use of relatively complex kits and costly dedicated machinery and the equally costly involvement of specialized technicians. This drawback makes the current known methods of preparation of PRP not adapted to a point-of-care use.

Further, the preparation of cells in view of cellular or tissue regeneration for use in transplantation, post-operative regeneration or for aesthetic purpose s faced to the long-term conservation problem of cells and tissues. Tissue or cell cryoconservation is generally used for the long-term maintaining of tissues or cells, notably platelets, but this technique has shown serious drawbacks and problems such as crystal formation, osmotic problems, aggregation, inhibition of protein synthesis ability, stress protein expression in response to thermal stress, etc. Therefore, tissue or cell cryoconservation is known to alter the cell viability and stability (*Agence française de sécurité sanitaire*, 2003; Arnaud et al., 1999, *Cryobiology*, 38, 192-199; Tablin et al., 2001, Cryobiology, 43(2), 114-23). Some of the cryoconservation side effects may be limited by the use of antifreezing agents such as DMSO or glycerol or other cryopreservatives (US 5, 5891, 617, Oh et al., *Cornea*, 26, 840-846) but the concentration of these agents has to be adapted to limit their toxicity and side effects.

Therefore, there is a need for new or alternative method of preparation of cells and tissues suited for use extemporaneously while preserving their integrity, notably in terms of growth factors secretion ability and viability.

SUMMARY

The invention relates to new cell preparation, a method of preparation of new cell preparations, a use of such cell preparations containing such as platelet cell preparations, optionally admixed with a cell extract, such as an autologous extract of keratinocytes, bone marrow cells, fibroblasts, periosteum or corneal cells, melanocytes and Langerhans cell; fat cells; muscle cells such as myoblasts and satellite cells; osteoblasts; chondrocytes; umbilical cord cells; Schwann cells or Achilles tendon cells.

The process for the preparation of a platelet concentrate composition according to the invention constitutes a reliable process collecting 95%+/−5 of the plasma cells, easy to use and cost effective (Borzini P. et al., in preparation).

In a first aspect, the present invention provides a process for the preparation of a platelet concentrate composition, comprising the steps of:
a) Centrifuging whole blood in a separator tube selected from:
   a glass separator tube containing a polyester-based thixotropic gel and a buffered sodium citrate solution at 0.10 M; and
   a polyethylene terephthalate separator tube containing a highly thixotropic gel formed by a polymer mixture and an anhydrous sodium citrate at 3.5 mg/mL;
b) Separating the enriched platelet rich plasma from the full plasma by removing half of the supernatant containing the platelet poor plasma;
c) Re-suspending the enriched plasma;
wherein the centrifugation step is performed at a force of or about 1500 g up to about 2000 g in a sufficient length of time to form a barrier between the plasma containing the platelets, the lymphocytes and the monocytes and the pellet containing the erythrocytes; the separation step b) is made by collecting the supernatant from atop of said barrier and wherein the enriched plasma is enriched in leucocytes, thrombocytes and adhesion proteins (for example, fibronectin) as compared to native whole blood.

In a second aspect, the present invention provides an isolated platelet concentrate composition comprising:
a) plasma;
b) platelets at a concentration of at least $300 \times 10^9$ cells/L;
c) white blood cells at a concentration of at least $7.0 \times 10^9$ cells/L;
d) fibrinogen at a concentration of at least 3 mg/L;
and wherein the erythrocyte concentration is less than $0.6 \times 10^{12}$ cells/L.

In a third aspect, the present invention provides a wound healant composition comprising:
a) plasma;
b) platelets at a concentration of at least $300 \times 10^9$ cells/L;
c) white blood cells at a concentration of at least $7.0 \times 10^9$ cells/L;
d) fibrinogen at a concentration of at least 3 mg/L;
e) coagulation activator in a vol. ratio (platelet concentrate: coagulation activator) of about 10:1 to about 10:3;
f) optionally an autologous cell extract, such as an extract of keratinocytes, bone marrow cells, osteoblasts; chondrocytes, fibroblasts, periosteum or corneal cells, melanocytes and Langerhans cell; fat cells; muscle cells such as myoblasts and satellite cells; umbilical cord cells; Schwann cells, tendon cells or pancreas islet cells;
and wherein the erythrocyte concentration is less than $0.6 \times 10^{12}$ cells/L.

In a fourth aspect, the present invention provides a process for the preparation of a wound healant composition comprising:
a) Providing a platelet concentrate of the invention;
b) Admixing the platelet concentrate with a coagulation activator in a vol. ratio (platelet concentrate:coagulation activator) of about 10:1 up to about 10:3;
c) Optionally admixing autologous cell extract, such as extract of keratinocytes, bone marrow, fibroblasts, periosteum or corneal cells, melanocytes and Langerhans cell; fat cells; muscle cells such as myoblasts and satellite cells; osteoblasts; chondrocytes; umbilical cord cells; Schwann cells or Achilles tendon cells.

In a fifth aspect, the present invention provides a device for the preparation of a platelet concentrate from whole blood comprising a separator tube wherein the separator tube is selected from:
a glass separator tube containing a polyester-based thixotropic gel and a buffered sodium citrate solution at 0.10 M; and
a polyethylene terephthalate separator tube containing a highly thixotropic gel formed by a polymer mixture and an anhydrous sodium citrate at 3.5 mg/mL;
characterised in that the device has an inlet for introducing said whole blood, is held in a vacuum intended to aspirate the whole blood sample, is sterile, has a usable vacuum of or about 8 to about 10 mL and is suitable for undergoing centrifugation.

In a sixth aspect, the present invention provides a use of a platelet concentrate according to the invention for the manufacture of a medicament for healing of wounds or for promoting bone or periodontum growth and/or bone and/or tissue regeneration.

In a seventh aspect, the present invention provides a use of a platelet concentrate according to the invention for the manufacture of a cosmetic preparation for use as anti-aging agent or skin repairing agent such as a scar repairing agent, a wrinkle filling and/or repairing agent.

In an eighth aspect, the present invention provides a pharmaceutical composition comprising platelet concentrate according to the invention and a pharmaceutically acceptable carrier.

In a ninth aspect, the present invention provides a cosmetic composition comprising platelet concentrate according to the invention and a cosmetically acceptable carrier.

In a tenth aspect, the present invention provides an implantable device for use in tissue regeneration therapy comprising:
(a) a permeable core comprising a platelet concentrate of the invention; and
(b) an external jacket surrounding said core, said jacket comprising a biocompatible material, preferably bioresorbable.

In an eleventh aspect, the invention provides a kit adapted for tissue regeneration comprising a separator tube according to the invention, phlebotomy accessories for the preparation of the wound healant according to the invention and an applicator device (e.g. a double syringe) for the simultaneous dispensation onto the wound of the platelet concentrate according to the invention and a coagulation activator.

In a twelfth aspect, the invention provides a method for promoting wound healing and/or sealing and/or tissue and/or bone regeneration in a wound of a human or a lower animal comprising:
a) Providing a wound healant according to the invention;
b) Applying a therapeutically effective amount of the said wound healant to a wound, a damaged tissue or a damaged bone.

In a thirteenth aspect, the invention provides a method for inducing periodontal regeneration in a wound or a periodontal defect of a mammal with periodontal disease or other condition requiring periodontal regeneration comprising:
a) Providing a wound healant according to the invention;
b) Applying a therapeutically effective amount of the said wound healant to the said wound or said periodontal defect or cavity;
c) Optionally inserting a periodontal barrier, wherein the barrier is positioned between the gingival tissue and the wound treated according to steps a) and b) and the said barrier is selected from a membrane, a biodegradable polymer and/or a biocompatible porous material;
d) Closing the wound.

In a fourteenth aspect, the invention provides a method for promoting skin regeneration in a scar or a wrinkle from human or lower animal comprising:
a) Providing a wound healant according to the invention;
b) Filling the skin scar or wrinkle line with the said wound healant.

In a fifteenth aspect, the present invention provides a process for the preparation of a cell composition, comprising the steps of:
(a) Centrifuging whole blood in a separator tube selected from:
  a glass separator tube containing a polyester-based thixotropic gel and a buffered sodium citrate solution at 0.10 M; and
  a polyethylene terephthalate separator tube containing a highly thixotropic gel formed by a polymer mixture and an anhydrous sodium citrate at 3.5 mg/mL;
(b) Optionally separating the enriched platelet rich plasma from the full plasma by removing half of the supernatant containing the platelet poor plasma;
(c) Re-suspending the enriched plasma;
(d) Providing a cell extract such as an extract of dermal cells such as keratinocytes, fibroblasts, melanocytes and Langerhans cell; fat cells; bone marrow cells; muscle cells such as myoblasts and satellite cells; osteoblasts; chondrocytes; periosteal membrane cells; corneal cells; umbilical cord cells; Schwann cells, tendon cells or pancreas islet cells;
(e) Admixing the platelet concentrate obtained under step (c) with the cell extract obtained in (d);
wherein the centrifugation step a) is performed at: a force of or about 1500 g up to about 2000 g in a sufficient length of time to form a barrier between the plasma containing the platelets, the lymphocytes and the monocytes and the pellet containing the erythrocytes; the separation step b) is made by collecting the supernatant from atop of said barrier and wherein the enriched plasma is enriched in leucocytes, thrombocytes and adhesion proteins (for example, fibronectin) as compared to native whole blood.

In a sixteenth aspect, the present invention provides a process for the preparation of a wound or tissue healing composition, comprising the steps of:
a) Centrifuging whole blood in a separator tube selected from:
  a glass separator tube containing a polyester-based thixotropic gel and a buffered sodium citrate solution at 0.10 M; and
  a polyethylene terephthalate separator tube containing a highly thixotropic gel formed by a polymer mixture and an anhydrous sodium citrate at 3.5 mg/mL;
b) Optionally separating the enriched platelet rich plasma from the full plasma by removing half of the supernatant containing the platelet poor plasma;
c) Re-suspending the enriched plasma;
d) Admixing the platelet concentrate obtained under step (c) with a coagulation activator in a vol. ratio (platelet concentrate:coagulation activator) of about 10:1 up to about 10:3;
e) Providing a cell extract such as an extract of dermal cells such as keratinocytes, fibroblasts, melanocytes and Langerhans cell; fat cells; bone marrow cells; muscle cells such as myoblasts and satellite cells; osteoblasts; chondrocytes; periosteal membrane cells; corneal cells; umbilical cord cells; Schwann cells, tendon cells or pancreas islet cells;
f) Admixing the platelet concentrate admixture obtained under step (d) with the cell extract obtained in (e);
wherein the centrifugation step is performed at a force of or about 1500 g up to about 2000 g in a sufficient length of time to form a barrier between the plasma containing the platelets, the lymphocytes and the monocytes and the pellet containing the erythrocytes; the separation step b) is made by collecting the supernatant from atop of said barrier and wherein the enriched plasma is enriched in leucocytes, thrombocytes and adhesion proteins (for example, fibronectin) as compared to native whole blood.

In a seventeenth aspect, the present invention provides an isolated cell composition comprising:
a) plasma;
b) platelets at a concentration of at least $300 \times 10^9$ cells/L;
c) white blood cells at a concentration of at least $7.0 \times 10^9$ cells/L;
d) fibrinogen at a concentration of at least 3 mg/L;

e) a cell extract, such as an extract of dermal cells such as keratinocytes, fibroblasts, melanocytes and Langerhans cell; fat cells; bone marrow cells; muscle cells such as myoblasts and satellite cells; osteoblasts; chondrocytes; periosteal membrane cells; corneal cells; umbilical cord cells; Schwann cells, tendon cells or pancreas islet cells wherein cells are at a concentration of about $10^5$ to about $10^6$ cells/L or a concentration of about $10^5$ to about $10^6$ cells/ml of plasma or enriched plasma; and wherein the erythrocyte concentration is less than $0.6 \times 10^{12}$ cells/L.

In an eighteenth aspect, the present invention provides an isolated cell composition comprising:
a) plasma;
b) platelets at a concentration of at least $300 \times 10^9$ cells/L;
c) white blood cells at a concentration of at least $7.0 \times 10^9$ cells/L;
d) fibrinogen at a concentration of at least 3 mg/L;
e) coagulation activator in a vol. ratio (platelet concentrate: coagulation activator) of about 10:1 to about 10:3;
f) a cell extract, such as an extract of dermal cells such as keratinocytes, fibroblasts, melanocytes and Langerhans cell; fat cells; bone marrow cells; muscle cells such as myoblasts and satellite cells; osteoblasts; chondrocytes; periosteal membrane cells; corneal cells; umbilical cord cells; Schwann cells, tendon cells or pancreas islet cells wherein cells are at a concentration of about $10^5$ to about $10^6$ cells/L or at a concentration of about $10^5$ to about $10^6$ cells/ml of plasma or enriched plasma;
and wherein the erythrocyte concentration is less than $0.6 \times 10^{12}$ cells/L.

In a nineteenth aspect, the invention provides a wound or tissue healing composition comprising an isolated cell composition according to the invention.

In a twentieth aspect, the invention provides a method for promoting wound healing and/or sealing and/or regeneration of a tissue and/or a cartilage and/or a bone and/or a nerve in a human or a lower animal comprising:
a) Providing a wound or tissue healing composition or a cell composition according to the invention;
b) Applying a therapeutically effective amount of the said a wound or tissue healing composition or cell composition to a wound, a damaged tissue or a damaged cartilage or a damaged bone.

In a twenty-first aspect, the invention provides a method for increasing adipose tissue volume in a mammal with a dermal fat graft or other condition requiring adipose tissue regeneration comprising:
a) Providing a fat cell composition according to the invention;
b) Applying a therapeutically or cosmetically effective amount of the said fat cell composition to the dermal fat graft or the adipose tissue requiring adipose tissue regeneration;
c) Optionally inserting a surgical flap or implant, wherein the surgical flap or implant, is positioned in the site requiring regeneration or volumetric amplification and the said surgical flap or implant comprises a combination of a fat cell preparation according to the invention and plasma or enriched plasma material.

In a twenty-second aspect, the invention provides a method for inducing myocardial regeneration in a mammal with myocardial deficiency or other condition requiring myocardial regeneration tissue regeneration comprising:
a) Providing a muscle cell or a bone marrow cell composition according to the invention;
b) Applying a therapeutically effective amount of the said muscle cell composition to the myocardial tissue requiring regeneration.

In a twenty-third aspect, the invention provides a method for inducing corneal regeneration in a mammal with corneal deficiency or other condition requiring corneal regeneration comprising:
a) Providing a cornea cell composition according to the invention;
b) Applying a therapeutically effective amount of the said corneal cell composition to the corneal tissue requiring regeneration.

In a twenty-fourth aspect, the invention provides a method for inducing articular or cartilage regeneration in a mammal with articular or cartilage deficiency or other condition requiring articular or cartilage tissue regeneration comprising:
a) Providing a chondrocyte cell or bone marrow cell composition according to the invention;
b) Applying a therapeutically effective amount of the said chondrocyte cell composition to the articular or cartilage tissue requiring regeneration;
c) Optionally inserting a surgical flap or implant, wherein the surgical flap or implant, is positioned in the defect of the cartilage or under a periosteal patch, and the said surgical flap or implant comprises a combination of a chondrocyte or bone marrow cell composition according to the invention and plasma or enriched plasma material.

In a twenty-fifth aspect, the invention provides a method for promoting skin regeneration in a scar, a wrinkle or a fat deficiency from human or lower animal comprising:
a) Providing a wound or tissue healant or a cell composition according to the invention;
b) Filling the skin scar, wrinkle line or fat deficiency with the said wound or tissue healant or cell composition according to the invention.

In a twenty-sixth aspect, the invention provides a method for inducing peripheral nerve regeneration in a mammal with peripheral nerve damage, nerve suture or spinal cord injury or other condition requiring peripheral nerve regeneration comprising:
a) Providing a Schwann cell composition according to the invention;
b) Applying a therapeutically effective amount of the said Schwann cell composition to the peripheral nerve requiring regeneration.

In a twenty-seventh aspect, the invention provides a method for inducing bone regeneration in a mammal with bone damage, bone deficiency or other condition requiring bone regeneration comprising:
a) Providing a bone marrow cell or osteoblast cell composition according to the invention;
b) Applying a therapeutically effective amount of the said bone marrow cell or osteoblast cell composition to the bone requiring regeneration.

In a twenty-eighth aspect, the invention provides a method for the treatment of type I diabetes, insulin-dependent diabetes or hyperglycaemia in a mammal comprising:
a) Providing a pancreas islet cell composition according to the invention;
b) Applying a therapeutically effective amount of the said pancreas islet cell composition to the patient, for example by injection.

In a twenty-ninth aspect, the invention provides a method for the treatment of urinary incontinence in a mammal or other condition requiring bladder regeneration comprising:

a) Providing a myoblast cell composition according to the invention;
b) Applying a therapeutically effective amount of the said myoblast cell composition to the bladder neck requiring regeneration.

In a thirtieth aspect, the invention provides a method for the treatment of anal incontinence in a mammal or other condition requiring anal muscle regeneration comprising:
a) Providing a myoblast cell composition according to the invention;
b) Applying a therapeutically effective amount of the said myoblast cell composition to the para-anal area requiring regeneration.

In a thirty-first aspect, the invention provides a method for the treatment of reflux oesophagitis or gastro-oesophageal reflux disorders in a mammal or other condition requiring oesophageal sphincter regeneration comprising:
a) Providing a myoblast cell composition according to the invention;
b) Applying a therapeutically effective amount of the said myoblast cell composition to the oesophageal sphincter requiring regeneration.

In a thirty-second aspect, the present invention provides a use of a cell preparation according to the invention for the manufacture of a medicament for healing of wounds or tissues or for promoting bone or periodontum growth and/or bone and/or tissue regeneration such as skin, cartilage, muscle, tendon, adipose tissue, cornea, peripheral nerves, spine or bone regeneration.

In a thirty-third aspect, the present invention provides a use of a cell composition according to the invention for the manufacture of a cosmetic preparation for use as anti-aging agent or skin repairing agent such as scar repairing agent, lipoatrophy repairing agent or wrinkle filling and/or repairing agent.

In a thirty-fourth aspect, the present invention provides a pharmaceutical composition comprising a cell composition according to the invention and a pharmaceutically acceptable carrier.

In a thirty-fifth aspect, the present invention provides a cosmetic composition comprising cell composition according to the invention and a cosmetically acceptable carrier.

In a thirty-sixth aspect, the present invention provides an implantable device for use in tissue regeneration therapy comprising:
a) a permeable core comprising a cell composition of the invention; and
b) an external jacket surrounding said core, said jacket comprising a biocompatible material, preferably bioresorbable.

The uses, methods and compositions according to the invention are useful in the regeneration and/or rejuvenation of tissues, bones and/or cartilages. The uses, methods and compositions according to the invention are particularly useful in the treatment of diabetic neuropathic ulcers or decubitus sores; bone and cartilage damages such as deep joint cartilage or chondral damages such as surgical repair of torn tendons; arthritis in joint caused by traumas or by aging; rotator cuff disorders; non-healing wounds such as vasculitis induced wounds, for example in lower equine limb; periodontal diseases; implant surgery; cardiac muscle damages such as in chronic cardiac failure, heart failure, ischemic and non-ischemic disorders, cardiomyopathy; gastro-oesophageal reflux disease; anal or urinary incontinence; facial surgery such as facial surgery induced alopecia (alopecia due to hair follicle loss in the side burn areas), face-lift surgery (rhytidectomy), rhinoplasty, dermal fat grafts (in the treatment of facial augmentation, congenital hemiatrophy of the face such as congenital cartilage nose atrophy and lipoatrophy such as in HIV/AIDS suffering patients, erosion and arthroscopy); wound healing complications such as after eyelid blepharoplasty; conical disorders such as corneal opacity such as those caused by chemical burns, affliction by Steven's Johnson syndrome and corneal ulcers; scarring of the cornea; dry eye syndrome; haematological diseases such as Thalassaemia; peripheral nerve damage, nerve suture and spinal cord injury; bone defects or disorders such as bone graft or bone fracture, skin damages or disorders such as acne (especially after dermabrasion treatment), burns, rubella or small pox scars, vitiligo, lipoatrophy, Kaposi's sarcoma, skin keloids or Dupuytren's palmar fibromatosis.

In another aspect, the uses, methods and compositions according to the invention are useful in the regeneration and/or rejuvenation of skin tissues, particularly in promoting and/or initiating skin regeneration such as reducing skin wrinkles, acne (especially after dermabrasion treatment), burns, rubella or small pox scars, vitiligo and lipoatrophy (e.g. anti-aging compositions and skin regeneration compositions), amelioration of nasolabial lines and treatment of skin damages or disorders such as skin burns, Kaposi's sarcoma, skin skeloids or Dupuytren's palmar fibromatosis and in the reduction of pain associated with skin and tissue regeneration.

DETAILED DESCRIPTION

Figure 1:
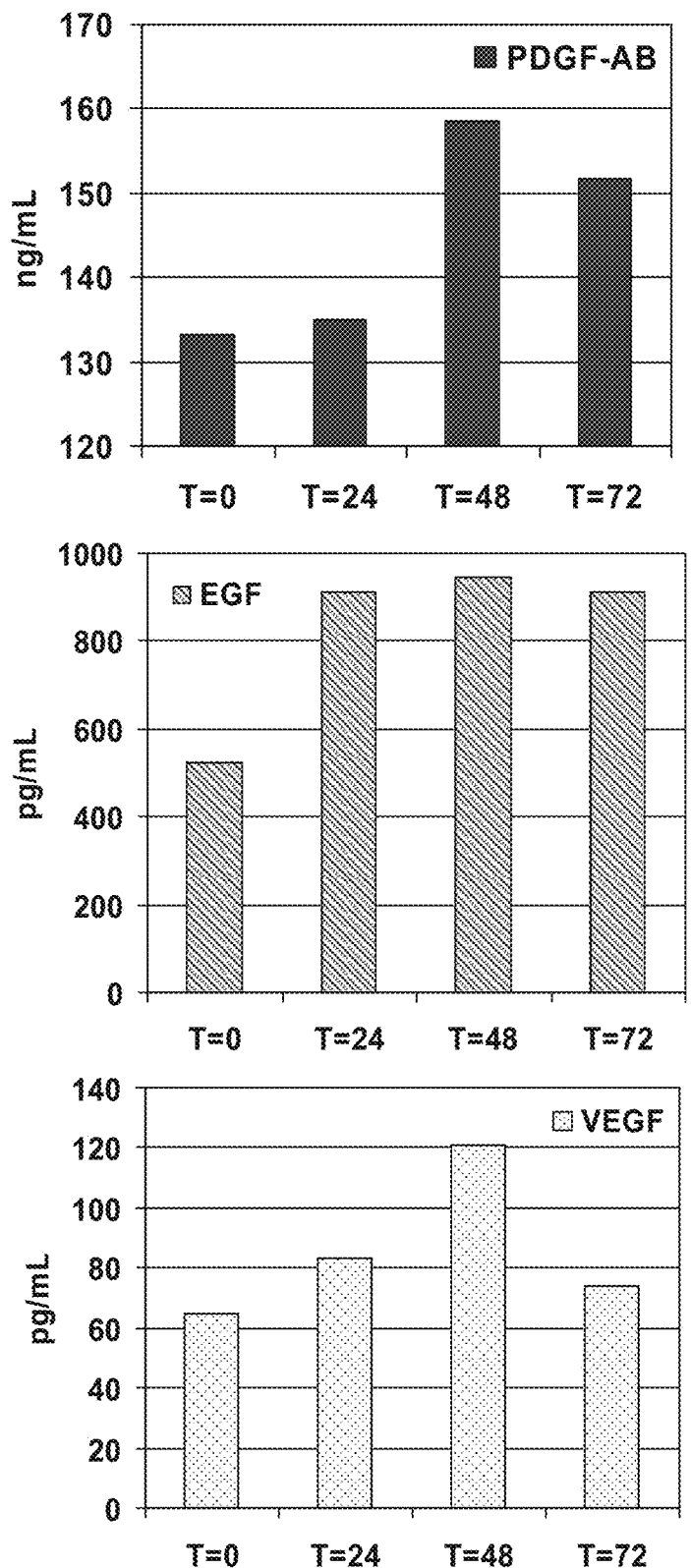
FIG. 1 is a schematic representation of the variation of concentration in growth factors (PDGF-AB, EGF and VEGF) of a platelet concentrate composition according to the invention versus time (T in hours) after the centrifugation step in the preparation process of the invention.

The following paragraphs provide definitions of the terms according to the invention and are intended to apply uniformly throughout the specification and claims unless an otherwise expressly set out definition provides a broader definition.

By the expression "thixotropic" is meant a gel that becomes more fluid as a result of agitation or pressure, i.e. a gel which viscosity is decreasing as a result of agitation or pressure. The term viscosity refers to those characteristics of the specified material(s) determining the degree of gelation, such as for example the firmness or hardness of the material, the degree to which the material resists flowing like a fluid. A thixotropic gel according to the invention comprising a polyester gel or a mixture thereof which is water insoluble and chemically inert to blood constituents which can be used in accordance with the invention. Typical thixotropic gels are used in blood cells separation for diagnostics and proteomics purposes.

By the expression "point-of-care" is meant all services provided to patients at the bedside.

By the expression "phlebotomy accessories" or "venipuncture accessories" is meant accessories that allow the puncture of a vein with a needle for the purpose of drawing blood.

By the expression "wound healant" or "wound sealant" or a "tissue healing composition" is meant an agent or a composition that is able to promote and/or increase the speed and/or quality of cicatrisation of a wound. Wound healants or sealants are able to promote tissue regeneration.

By the expression "wound" is meant any damaged tissue, for example following trauma or surgery. Wounds in mammals, include for examples bed sores, ulcers, lacerations and burns, graft sites (graft donor and acceptor sites), fistulas, periodontal tissue damages, diabetic non-healing wounds, consequences of traumas or any surgery act. In its general sense the expression is intended to also encompass skin damages where the skin surface presents some depression without necessarily a cut on its surface such as age-related tissue damages (e.g. wrinkles) and scars such as for example acne (especially after dermabrasion treatment) or rubella scars.

By the expression "PRP" is intended to mean a platelet-rich-plasma, preferably of human origin, more preferably autologous, prepared by the process of the invention in order to pellet and remove erythrocytes and concentrate the plasma in leucocytes, thrombocytes and adhesion proteins as compared to native whole blood.

By the expression "autologous" or "autogenic" or "autogenous" is intended a method of the invention using a single donor's blood and wherein the blood extracted from this donor is intended for use on the same donor. As opposed, "allogeneic" methods are using blood from one or more third patties for use on a donor ("homologous" or "heterologous"). An autologous product avoids some of the common problems associated with the use of biological materials from third parties, such as for example screening to assure that the donor was biologically or immunologically compatible with the patient and potential contamination with hepatitis, HIV, prion, Creutzfeldt-Jacob disease and the like.

By the expression "coagulation activator" is intended an agent that is able to trigger or activate coagulation. A coagulation activator comprises a thrombin activator and/or a fibrinogen activator.

By the expression "thrombin activator" is intended an agent that is able to activate thrombin and to trigger coagulation. Typical thrombin activators are certain cofactors such as sodium or calcium. In practicing this invention, thrombin activation preferably occurs in the presence of calcium ions. Calcium ions are generally added to the platelet concentrate as a salt solution to provide a final concentration generally of or about 0.1 mg/mL of platelet concentrate. Suitable calcium salts include, without limitation, $CaCO_3$, and $CaSO_4$. A preferred calcium salt for use in the invention is calcium chloride ($CaCl_2$). $CaCl_2$ is available as calcium chloride injection, USP 10% (Regen Lab, Switzerland).

By the expression "fibrinogen activator" is intended an agent that is able to activate the conversion of fibrinogen into fibrin and triggers the formation of the clot. Typical fibrinogen activators are thrombin or batroxobin. The term thrombin may include calcified thrombin, in particular, from or about 100 to about 10 units of thrombin per 1 mL of 10% of aqueous calcium chloride solution; it may include calcified bovine thrombin, allogeneic thrombin or recombinant human thrombin, preferably autologous thrombin. A fibrinogen activator can be an enriched thrombin composition such as thrombin compositions as described in U.S. Pat. No. 6,472,162 or an autologous thrombin serum according to the invention.

By the expression "therapeutically effective amount" is intended the amount or amounts of the constituent elements or combination thereof necessary to enhance wound healing such as, for example, the reduction in the volume or surface area of a wound, the increase in the amount of granulation tissue or other biological material facilitating collagen lay down, vascular in growth, fibroblast proliferation or overall healing; All of the versions of the invention described herein are assumed to have the therapeutically effect amount(s) of constituent substances, or combinations thereof.

By the expression "pharmaceutically acceptable carrier" is intended pharmaceutically acceptable additional ingredient such as stabilizers, antimicrobial agents, buffers, adjuvants, anaesthetics, corticosteroids and the like.

By the expression "cosmetically acceptable carrier" is intended cosmetically acceptable additional ingredient such as stabilizers, buffers, colouring agents, flavouring agents, adjuvants, and the like.

The compositions, uses and methods according to the invention are particularly useful in wound or tissue healing or regeneration treatments, especially the treatment of traumatic or surgical wounds such in the fitting and/or holding and/or sealing of native or prosthetic grafts (especially skin, bone grafts and/or dental prostheses or implants or the like, including also the graft donor site); treatment of vasculitis; ulcers such as diabetic neuropathic ulcers or decubitus sores; radiodermatitis (e.g. after irradiation on an epidermoidal skin carcinoma) and closing fistulas (such as for cyclists).

Further, the compositions, uses and methods according to the invention are particularly useful in the treatment of cardiac disorders, cardiac regeneration such as in the treatment of heart failure, chronic cardiac failure, ischemic and non-ischemic cardiac failure and cardiomyopathy.

Further, the compositions, uses and methods according to the invention are particularly useful in the treatment of urinary and/or anal incontinence.

Further, the compositions, uses and methods according to the invention are particularly useful in the treatment of reflux oesophagitis and/or gastro-oesophageal reflux disorder.

Further, the compositions, uses and methods according to the invention are particularly useful in the treatment of skin damages such as in skins damaged by radiations (radiodermatitis or sun damaged skin), aged skins or burned skins and/or in the amelioration of facial wrinkles, rhytids, acne (especially after dermabrasion treatment), burns, rubella or small pox scars, vitiligo, lipoatrophy or lipodystrophy, Kaposi's sarcoma, skin skeloids or Dupuytren's palmar fibromatosis and/or in skin rejuvenation treatments.

Further, the compositions, uses and methods according to the invention are particularly useful in the treatment of lipoatrophy such as in HIV/AIDS patients and in other congenital hemiatrophy of the face such as congenital cartilage nose atrophy.

Further, the compositions, uses and methods according to the invention are particularly useful in the treatment of bone, cartilage and articular disorders such as chondral damage, arthritis, cartilage and/or bone injury such as deep cartilage damage and/or erosion and/or arthroscopy, tendon torn and rotator cuff in shoulder.

Further, the compositions, uses and methods according to the invention are particularly useful in the treatment of hematological diseases such as Thalassaemia.

Further, the compositions, uses and methods according to the invention are particularly useful in the treatment of corneal disorders such as dry eye syndrome; corneal opacity such as those caused by chemical burns, affliction by Steven's Johnson syndrome; scarring of the cornea and corneal ulcers.

Further, the compositions, uses and methods according to the invention are particularly useful in the treatment of peripheral nerve damage, nerve suture and spinal cord injury.

Further, the compositions, uses and methods according to the invention are particularly useful in the treatment of type1 diabetes, insulin-dependent diabetes and/or hyperglycaemia.

Further, the compositions, uses and methods according to the invention are particularly useful in the treatment of bone defects or disorders such as bone graft or bone fracture.

The use of the resulting composition the invention can be further modified before application and according to the therapeutic objective.

Compositions of the invention can be used together with bone filling materials, especially resorbable filling materials such as hydroxyapatite (calcium phosphate ceramic used as a biomaterial) or demineralised bone, or used as a mixture with bone extracts in a process for the regrowth of bone for example in craniofacial and orthopaedic procedures.

Compositions of the inventions may be used as a wound sealant in plastic surgery including burn grafting and other free skin graft applications, for example in oncology for favouring tissue regeneration, including speeding (neo)vascularization.

The compositions according to the invention are particularly useful in wound healing treatments at the skin graft donor site. The removal of a skin graft on a healthy skin creates a new wound at the donor's site which normally heals spontaneously between 12 to 14 days. However, this cicatrisation is extremely demanding for the body, especially if the donor site is broad or the person is less resistant (e.g. burn victims, people suffering from multiple traumas, people treated with corticoids, children or elderly) and the energetic losses are even increased by the loss in minerals, trace elements and proteins induced by the fluid losses from the new wound. In addition, important pain during the first 8 days is often present on the graft donor's site. Pain reduction treatments are often used such as the use of analgesics (e.g. morphine) and/or hydrocellular wound dressings, however pain remains present, especially during the dressing change that occurs imperatively within 48 hours up to 1 week after the graft removal. In addition, the hydrocellular wound dressings have the drawbacks not only to be rather expensive but also by maintaining humidity on the wound, to prevent its drying, to increase the wound deepness, to favour the outbreak of bacterial infections and to lead to nonesthetic scars. Therefore, a stimulation of the skin graft donor site healing is very desirable.

Compositions of the invention are particularly adapted to chronic wounds that may lack sufficient blood circulation to facilitate the wound healing cascade.

The compositions and methods according to the invention may be also used in the treatment of periodontal disease where a loss and/or a damage of the periodontal tissues is observed, such a treatment comprising for example placing at the periodontal site or cavity in a human or a lower animal in need of periodontal tissue regeneration a composition according to the invention.

The compositions according to this invention are effective in eliminating or greatly reducing post-operative bleeding and extravasation or loss of serous or other fluid in these applications, in reducing the infection risk caused by most bacteria and/or enhances connective tissue formation compared to natural healing (i.e. no exogenous agents added) or to healing obtained through the use of other platelet concentrates prepared with known methods.

The compositions according to the invention are particularly useful in the preparation of pharmaceutical for promoting and/or initiating wound healing and/or tissue regeneration or for the preparation of cosmetic compositions for skin regeneration such as reducing skin wrinkles, acne (especially after dermabrasion treatment), rubella or small pox scars, vitiligo and lipoatrophy (e.g. anti-aging compositions and skin regeneration compositions).

The compositions of the present invention may be administered locally or injected in the wound or in or near to the grafted organ or injected subcutaneously. Local administration may be by injection at the site of injury or defect or by insertion or attachment of a solid carrier at the site, or by admixture with a cream or emulsion, or by inclusion in a tissue or paper or hydrogel carder, or by direct, topical application of the composition of the invention such as in the form of eye drops. Preferably, the compositions are readily syringable compositions. The mode of administration, the dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

The compositions of the present invention may be administered in combination with a co-agent useful in the treatment of tissue regeneration such as a healing agent, a wrinkle filler, an anti-aging agent such as an anti-aging vitamin complex, an antibacterial agent, antibiotic agent, an corticosteroid agent, an antalgic and analgesic agent, or an anesthetic agent like adrenaline, etc. . . . The invention comprises compositions combined with a co-agent useful in the treatment of tissue regeneration for simultaneous, separate or sequential use in tissue regeneration therapy such as wound healing, bone and periodontum growth repair.

The compositions of the invention, the device and procedures for the preparation of autologous platelet concentrates or cell compositions of the invention are particularly useful for therapeutic use, particularly as autogenous biological glue in a haemostatic system intended to accelerate the physiological process of tissue regeneration, for example in dental implantology, skin and bone surgery, cartilage and tendon surgery, corneal and peripheral nerve regeneration and cardiac surgery. The compositions of the invention, the device and procedures for the preparation of autologous platelet concentrates and cell composition of the invention are particularly useful for cosmetic use, particularly as autogenous rejuvenation material intended to be used for example as wrinkle, scar or fat deficiency filler, alone on in combination with at least one anti-aging agent.

The platelet concentrate of the invention may be combined with an autologous cell extract preparation such as for example keratinocytes, bone marrow cells, osteoblasts, chondrocytes, fibroblasts, periosteum, melanocytes and Langerhan's cell; fat cells; bone marrow cells; muscle cells such as myoblasts and satellite cells; periosteal membrane cells; corneal cells; umbilical cord cells; tendon cells or pancreatic islet cells, Keratinocytes can be harvested through a method described by Reinwald and Green, 1975, *Cell,* 6(3):331-43. Other mentioned cells can be harvested through methods described in *"Culture de cellules animales; méthologies-applications",* 2003, Ed. Barlovatz-Meimom and Adolphe, INSERM editions, Parts. Alternatively, cell extracts are derived from a cell bank or a cell culture or harvested as described in the Examples below.

The platelet concentrate and cell compositions of the invention have proven to be really beneficial in the acceleration and/or promotion of the healing process of wounds, even chronic unhealing wounds, leading to successful closures where weeks of conventional therapies had failed and achieving a decrease in infection risks, an improvement in patient's recovery and comfort, a reduction of medical care costs and a better aesthetic final result.

The compositions of the invention can of course be also prepared from plasma derived from several identified donors. The invention is not limited to autologous biological materials, such as collection of concentrated platelets from the wounded's own biological material. The invention encompasses the use of biological materials obtained from one or more third parties, who need not be of the same species as the patient whose wound is being treated with the wound healant composition described herein unless bio-incompatibility would result from the use of such third party biological materials.

In one embodiment, the invention provides a process for the preparation of a platelet concentrate composition or a cell composition as described herein.

In another embodiment, the present invention provides a device for the preparation of a platelet concentrate composition from whole blood as described herein.

In a further embodiment, is provided by the invention a process for the preparation of a platelet concentrate composition wherein the centrifugation step is performed at force between about 1'500 g and up to about 1'700 g for a time selected from about 3 min up to about 15 min, preferentially at 1'500 g for about 8 min.

In another further embodiment, is provided by the invention a process for the preparation of a platelet concentrate composition wherein the separator tube has an inlet for introducing said whole blood, is held in a vacuum intended to aspirate the whole blood sample, is sterile, has a usable vacuum of 8 to 10 mL and is suitable for undergoing centrifugation.

In another further embodiment, is provided by the invention a process for the preparation of a platelet concentrate composition wherein the separator tube is a polyethylene terephthalate separator tube containing a highly thixotropic gel formed by a polymer mixture and an anhydrous sodium citrate at 3.5 mg/mL.

In another embodiment, the present invention provides an isolated platelet concentrate composition obtainable from the process according to the invention.

In another embodiment, is provided by the invention an isolated platelet concentrate composition comprising:
a) plasma;
b) platelets at a concentration of at least $300 \times 10^9$ cells/L, preferably of at least $350 \times 10^9$ cells/L, more preferably of at least $400 \times 10^9$ cells/L;
c) white blood cells at a concentration of at least $7.0 \times 10^9$ cells/L, preferably of at least $8.0 \times 10^9$ cells/L;
d) fibrinogen at a concentration of at least 3 mg/L;
and wherein the erythrocyte concentration is less than $0.6 \times 10^{12}$ cells/L, preferably less than $0.5 \times 10^{12}$ cells/L.

In another embodiment, the present invention provides a wound or tissue healant composition comprising:
a) plasma;
b) platelets at a concentration of at least $300 \times 10^9$ cells/L, preferably of at least $350 \times 10^9$ cells/L, more preferably of at least $400 \times 10^9$ cells/L;
c) white blood cells at a concentration of at least $7.0 \times 10^9$ cells/L, preferably of at least $8.0 \times 10^9$ cells/L;
d) fibrinogen at a concentration of at least 3 mg/L;
e) a coagulation activator in a vol. ratio (platelet concentrate: coagulation activator) of about 10:1 to about 10:3;
f) optionally an autologous cell extract, such as extract of keratinocytes, bone marrow cells, fibroblasts, periosteum, melanocytes and Langerhans cell; fat cells; bone marrow cells; muscle cells such as myoblasts and satellite cells; osteoblasts; chondrocytes; periosteal membrane cells; corneal cells; umbilical cord cells; tendon cells or pancreatic islet cells;
and wherein the erythrocyte concentration is less than $0.6 \times 10^{12}$ cells/L, preferably less than $0.5 \times 10^{12}$ cells/L.

In another embodiment, is provided by the invention a process for the preparation of a wound or tissue healant composition as described herein.

In another further embodiment, is provided by the invention a process for the preparation of a wound or tissue healant composition wherein the coagulation activator which is admixed is 10% calcium chloride.

In another further embodiment, is provided by the invention a process for the preparation of a wound or tissue healant composition wherein the coagulation activator which is admixed under step b) is a thrombin enriched preparation. A method for preparing thrombin for use in a biological glue is described in U.S. Pat. No. 6,472,162 by the addition of 8 to 20% ETOH to a volume of plasma and this preparation may be used as a thrombin enriched preparation in the context of the invention. Alternatively, an autologous thrombin serum (ATS) can be used a thrombin enriched preparation in the context of the invention. An autologous thrombin serum according to the invention is obtained by a process comprising (i) the addition to a patient's whole blood sample (e.g. 8 mL) collected in a separator tube of the invention, a 10% of final volume of calcium chloride 10% (e.g. 1 mL) and a 10% of the final volume of a preparation of 95% v. ethanol solution (e.g. 1 mL) and (ii) precipitation for about 30 min at room temperature. After 30 min, a centrifugation at or about 1'500 g for about 8 to 10 min. In a further preferred embodiment, the thrombin enriched preparation and preferably the autologous thrombin serum is admixed under step b) directly on the wound.

In another further embodiment, is provided by the invention a process for the preparation of a wound or tissue healant composition according to the invention wherein a further step b') wherein the activated platelet-rich preparation composition (obtained by the admixing of the platelet concentrate with the said coagulation activator) obtained in step b) may be partially dehydrated by the contact of a wound dressing covered by a soft hydrophobic layer to avoid contamination with micro-strings from the dressing in order to obtain a semi-solid gel that can be manipulated by appropriate instruments, for example to fill a cavity or tissue deficiency, or as a growth matrix ("scaffold") while waiting for the reconstitution of the autogenous extracellular matrix.

The obtained wound or tissue healant is particularly useful in a method for inducing periodontal regeneration in a wound, a tissue or a periodontal defect or a cavity.

In another further embodiment, is provided by the invention a process for the preparation of a wound or tissue healant or cell composition wherein the cell extract is an extract of keratinocytes.

In another further embodiment, is provided by the invention a process for the preparation of a wound or tissue healant or cell composition wherein the cell extract is an autologous extract of keratinocytes.

In another further embodiment, is provided by the invention a process for the preparation of a wound or tissue healant or cell composition wherein the cell extract is an extract of skeletal muscle cells such as muscle progenitor cells or satellite stem cells.

In another further embodiment, is provided by the invention a process for the preparation of a wound or tissue healant or cell composition wherein the cell extract is an extract of fibroblasts.

In another further embodiment, is provided by the invention a process for the preparation of a wound or tissue healant or cell composition wherein the cell extract is an extract of adipocytes.

In another further embodiment, is provided by the invention a process for the preparation of a wound or tissue healant or cell composition wherein the cell extract is an extract of chondrocytes.

In another further embodiment, is provided by the invention a process for the preparation of a wound or tissue healant or cell composition wherein the cell extract is an extract of stem cells such as umbilical cord stem cells.

In another further embodiment, is provided by the invention a process for the preparation of a wound or tissue healant or cell composition wherein the cell extract is an extract of tendon cells.

In another further embodiment, is provided by the invention a process for the preparation of a wound or tissue healant or cell composition wherein the cell extract is an extract of periosteal membrane or gingival cells.

In another further embodiment, is provided by the invention a process for the preparation of a wound or tissue healant or cell composition wherein the cell extract is an extract of corneal cells.

In another further embodiment, is provided by the invention a process for the preparation of a wound or tissue healant or cell composition wherein the cell extract is an extract of bone marrow cells.

In another further embodiment, is provided by the invention a process for the preparation of a wound or tissue healant or cell composition wherein the cell extract is an extract of osteoblast cells.

In another further embodiment, is provided by the invention a process for the preparation of a wound or tissue healant or cell composition wherein the cell extract is an extract of Schwann cells.

In another further embodiment, is provided by the invention a process for the preparation of a wound or tissue healant or cell composition wherein the cell extract is an extract of pancreas islet cells.

In another further embodiment, the isolated platelet concentrate composition, the wound or tissue healant composition, the thrombin enriched serum and/or the cell extract of the invention is/are autologous.

In a further aspect, the present invention provides a kit adapted for tissue regeneration according to the invention wherein the kit further comprises separate vials containing ETOH and $CaCl_2$, syringe holders, clumper and a tip applicator with a dual exit.

In a further aspect, present invention provides a kit adapted for tissue regeneration according to the invention comprising two sterile blisters:
(1) one blister comprising accessories for the phlebotomy, separator tubes of the invention, vials of ETOH and $CaCl_2$ for the preparation of an autologous thrombin serum; and
(2) a second blister comprising accessories for two syringe holders and clumper, and tip applicator with a dual exit.

In another embodiment, the invention provides a process for the preparation of a cell composition according to the invention wherein the cell extract provided under step d) or e) is obtained by a process comprising the steps of:
(A) Providing the said cells in a platelet concentrate according to the invention;
(B) Optionally culturing the cells;
(C) Re-suspending the cultured cells obtained under step (B) into a platelet concentrate according to the invention.

In a further embodiment, the invention provides a process for the preparation of a cell composition according to the invention wherein the cell expansion under step (A) is performed in a platelet concentrate according to the invention such as the final concentration in platelets comprised between about 5% and about 40% of the volume of the culture medium.

In another further embodiment, the invention provides a process for the preparation of a cell composition according to the invention wherein the cell culture step (B) comprises at least one step of plating the cells, for example on a cell culture surface such as a Petri dish or a culture flask.

In another further embodiment, the invention provides a process for the preparation of a cell composition according to the invention comprising at least one further step of harvesting the cells after the cell culture step (B).

In another further embodiment, the invention provides a process for the preparation of a cell composition according to the invention wherein the cell culture step (B) is performed at 37° C.

In another further embodiment, the invention provides a process for the preparation of a cell composition according to the invention wherein the cell culture step (B) is performed under a gas flow comprising oxygen or air and carbon dioxide, typically the gas flow comprises 95% of oxygen or air and 5% carbon dioxide.

In another further embodiment, the invention provides a process for the preparation of a cell composition according to the invention wherein the cell culture step (B) is lasting for about 3 up to about 4 weeks.

In another further embodiment, the invention provides a process for the preparation of a cell composition according to the invention wherein during the cell culture step (B), the cell culture medium is regularly changed during incubation, typically every about 3 days.

In another further embodiment, the invention provides a process for the preparation of a cell composition according to the invention wherein the cell culture step (B), comprises at least one exposure step of the cells to visible light, typically at about 633 nm, during about 10 minutes. In another aspect, the exposure step to visible light is repeated once a week during cell incubation.

In another further embodiment, the invention provides a process for the preparation of a cell composition according to the invention wherein the cell composition is a keratinocyte or fibroblast cell composition and the cell culture step (B), comprises at least one exposure step of the cells to visible light, typically at about 633 nm, during about 10 minutes. In another aspect, the exposure step to visible light is repeated once a week during cell incubation.

In another further embodiment, the invention provides a process for the preparation of a cell composition according to the invention wherein the cell culture step (B), comprises at least one step of addition of diluted platelet concentrate according to the invention such as the final concentration in platelets comprised between about 5% and about 40% of the volume of the culture medium.

In another further embodiment, the invention provides a process for the preparation of a cell composition according to the invention wherein the cell composition is a keratinocyte or fibroblast cell composition and the cell culture step (B), comprises at least one step of addition of diluted platelet concentrate according to the invention such as the final concentration in platelets comprised between bout 5% and about 40% of the volume of the culture medium.

In another embodiment, the present invention provides an isolated cell composition obtainable from a process according to the invention.

In another embodiment, the present invention provides an isolated cell composition, wherein the isolated cell composition is a fat cell composition such as an adipocyte cell composition.

In another embodiment, the present invention provides an isolated cell composition, wherein the isolated cell composition is a muscle cell composition such as a myoblast cell or a satellite stem cell composition.

In another embodiment, the present invention provides an isolated cell composition, wherein the isolated cell composition is a corneal cell composition.

In another embodiment, the present invention provides an isolated cell composition, wherein the isolated cell composition is a cartilage cell composition, such as a chondrocyte cell composition.

In another embodiment, the present invention provides an isolated cell composition, wherein the isolated cell composition is a skin cell composition, such as a fibroblast cell or keratinocyte cell composition.

In another embodiment, the present invention provides an isolated cell composition, wherein the isolated cell composition is a periosteal membrane or gengival cell composition.

In another embodiment, the present invention provides an isolated cell composition, wherein the isolated cell composition is a tendon cell composition, such as tendon cell composition.

In another embodiment, the present invention provides an isolated cell composition, wherein the isolated cell composition is a stern cell composition, such as an umbilical cord stem cell composition.

In another embodiment, the present invention provides an isolated cell composition, wherein the isolated cell composition is a bone marrow cell composition.

In another embodiment, the present invention provides an isolated cell composition, wherein the isolated cell composition is a Schwann cell composition.

In another embodiment, the present invention provides an isolated cell composition, wherein the isolated cell composition is a pancreas islet cell composition.

In another embodiment, the present invention provides an isolated cell composition, wherein the isolated cell composition is an osteoblast cell composition.

In another embodiment, the present invention provides an isolated cell composition, wherein cells are at a concentration of about $3 \times 10^5$ to about $10^6$ cells/ml of plasma or enriched plasma.

In another embodiment, the present invention provides compositions, methods and uses for promoting wound sealing and/or tissue and/or bone regeneration in a wound of a human or a lower animal as described herein.

In another further embodiment, the present invention provides compositions, methods and uses for promoting wound sealing and/or tissue and/or bone regeneration in a wound of a mammal, preferably human.

In another embodiment, the present invention provides compositions, methods and uses for inducing periodontal regeneration in a wound or a periodontal defect of a mammal with periodontal disease or other condition as described herein.

In another further embodiment, the present invention provides a method for inducing periodontal regeneration in a wound or a periodontal defect or cavity of a mammal with periodontal disease or other condition wherein the mammal is human.

In another further embodiment, the present invention provides a method for inducing periodontal regeneration in a wound or a periodontal defect or cavity according to the invention wherein the said therapeutically effective amount of the said wound or tissue healant composition is applied in a form of semi-solid gel or a growth matrix to the said wound or said periodontal defect or cavity such as described for example in Garg et al., 2000, *Dental Implantology Update*, 11(6), 41-44.

In another embodiment, the present invention provides a method for promoting skin tissue regeneration in a scar or wrinkle as described herein.

In another embodiment, the present invention provides a method for inducing myocardial regeneration according to the invention, wherein the said therapeutically effective amount of the said muscle cell composition according to the invention is injected into the myocardium, typically into the left ventricule myocardium. Injection can be made as direct injection or multiple catheter injection. Myoblasts or satellite cells can be engineered ex vivo as described in the present description onto a de-epithelised and UV irradiated human biological amnion and biocomposite construct, as a monolayer in the present description. The amnion is then sutured to the ischaemic epicardium in order to repopulate the underlying tissue with stem cells, in order to improve the contractile power of the ventricular wall and myocytes.

In another embodiment, the present invention provides a method for inducing myocardial regeneration according to the invention, wherein the said therapeutically effective amount of the said muscle cell composition according to the invention is injected into the myocardium, together with a therapeutically effective amount of fibroblast cell composition according to the invention such as the ratio fibroblast/myoblast is of about 30:70.

In another embodiment, the present invention provides a method for inducing myocardial regeneration according to the invention, wherein the said therapeutically effective amount of the said muscle cell composition according to the invention is applied on the ventricular surface in the form of an amnion patch preferably incubated into a myoblast and satellite stem cell composition according to the invention.

In another embodiment, the present invention provides a method for inducing corneal regeneration according to the invention, wherein the said therapeutically effective amount of the said corneal cell composition according to the invention is applied to the corneal tissue in the form of an amnion patch preferably spread on a dissolvable contact lens.

Said method of treating a wound, a tissue or a disease may include the use of any of the compositions described herein;

it may also include the use of any composition made by any of the methods described herein.

The methods, the devices and the kit according to the invention present the advantages to provide a time-effective and relatively low-cost way of obtaining platelet concentrates in a single operation that is easy to implement and adapted to a point-of-care application. The methods of the invention present the advantage to not only lead to enriched preparations wherein the platelets are concentrated in such a high yield that is not obtained by known methods but also wherein the content in erythrocytes is much lower than those obtained by known methods for the preparation of PRP. The compositions of the invention present the advantage of having a higher content in platelets, a lower content in erythrocytes than PRP obtained by known methods and completely maintained properties for its subsequent therapeutic use in-vivo. More specifically, the ability of the platelets to release the principal growth factors involved in tissue regeneration (PDGF, TGF-β, IGF, VEGF and EGF) at levels for several days (or the 7-10 day life span of thrombocytes) is maintained.

In addition, to the extent the compositions of the invention are made from autologous blood, the invention described herein reduces the disease transmission and immunoreaction risks associated with the use of the treatment materials made from biological materials obtained from one or more third parties.

The invention therefore provides an improved biological wound healing and tissue regenerating material, preferably autologous, promoting tissue such as skin, cartilage and bone regeneration, especially cicatrisation and/or rejuvenation. The benefits of the invention comprise a simple and rapid method of preparation of improved wound healing and tissue regenerating materials adapted to point-of-care services and which proved to decrease the healing time, associated pain and medical costs. Further, the wound healing and tissue regenerating material decreases the graft rejection risks and improves graft success rates. Further, the improved wound healing and tissue regenerating materials lead to scars having a much better aesthetic final aspect and to the durable filling of scars and wrinkles.

Typically, cell extracts are obtained from a tissue biopsy wherein the biopsy is preferably performed the day before the mixture with the platelet concentrate under step a). The size of the biopsies is adapted to the aimed therapeutic purpose and the types of cells used in the preparation of the cell composition according to the invention. Examples of biopsies are given in the Examples below for different types of tissues.

Examples illustrating the invention will be described hereinafter in a more detailed manner and by reference to the embodiments represented in the Figures.

EXAMPLES

The following abbreviations refer respectively to the definitions below:
ATS (autologous thrombin serum); BU (Baxothrobin unit); DMEM (Dulbecco's minimum essential medium); DMSO (Dimethyl Sulfoxide); EC (Enriched clot); FCS (fetal calf serum); HT (healing time); IU (International Unit); PBS (Phosphate Buffered Saline); PET (polyethylene terephthalate); PRP (platelet-rich plasma); PPP (platelet-poor plasma); USP (United States Pharmacopoeia); cm (centimeter); dL (decilitre); g (gram); Gy (gray); J (Joule); L (liter); min (minute); mm (millimetre); M (molar); mL (millilitre); nm (nanometre); rpm (Rotation per minute); Vol. (volume).

General Procedures & Conditions

To determine the effectiveness of compositions of the invention in promoting wound healing and/or bone and/or tissue regeneration, the following experiments are performed.

Whole human blood samples are collected in a separator tube according to the invention. A separator tube according to the invention is for example an approximately 15 mL glass tube (16 mm diameter and 130 mm in length) containing 3 mL of polyester-based thixotropic gel as well as 1 mL of sodium citrate solution at 0.1 M and containing a usable vacuum of or about 8.5 mL. This separator tube constitutes a ready-to-use device for the preparation of a platelet concentrate composition of the invention (also called RegenTHT™ (Thrombocyte Harvesting Tube) from Regen Lab, Switzerland).

Another example of a separator tube according to the invention is a tube of approximately 10 mL in PET (polyethylene terephthalate) containing 1 mL of a thixotropic gel comprising a polymer mixture and anhydrous sodium citrate deposited on the inner surface of the tube by spraying (about 3.5 mg per mL of blood) and containing an usable vacuum of or about 8 mL, constitutes a ready-to-use device for the preparation of a platelet concentrate according to the invention (also called RegenBCT™ (Blood Cell Therapy) from Regen Lab, Switzerland).

These tubes are sterilized by irradiation (such as prescribed by ISO 11137, UNI EN ISO 11737-2, UNI EN 552, UNI EN 556) and hermetically sealed by a traditional cap such mottled bromobutyl conventional rubber stopper for the glass tube and a chlorobutyl stopper having a polyethylene cover for the operator safely.

Then, the separator tube is centrifuged at or about 1'500 g up to or about 2'000 g, for about 3 to 10 min, i.e. of or about 2'500 rpm up to or about 3'800 rpm with a centrifuge with a swinging rotor, having a radius of 20 cm, in case of a centrifuge having a rotor with a fixed angle of about 45°, the centrifugation time should last for at least about 15 min.

After centrifugation, the platelet concentrate is collected for use in therapeutic or cosmetic applications of the invention or for the preparation of further compositions containing the obtained platelet concentrate through the mixture with further agents such as cell extracts, preferably autologous (e.g. keratinocytes, fibroblasts, bone marrow cells, osteoblasts, chondrocytes, myoblasts, conical cells, schwann cell, fat cells, umbilical cord stem cells, tendon cells, pancreas islet cells, ligament and gingival cells, periosteal membrane cells) and/or bone substitutes and/or coagulation activators.

For the therapeutic applications, a kit according to the invention adapted for tissue regeneration is used wherein the kit (also called RegenKit™) comprises two sterile blisters comprising:
  one blister (RegenPRP™) comprising accessories for the phlebotomy, separator tubes of the invention (RegenTHT™ or RegenBCT™), optionally vials of ETOH and CaCl$_2$ for the preparation of an autologous thrombin serum (RegenATS™).
  one blister (RegenApplicator™) comprising two syringes (e.g. 1 mL and 1 or 3 mL), holders and damper and a tip applicator with a dual exit.

For the preparation of cell compositions, according to the invention, the cells are prepared according to the general protocol as follows:

a) Biopsy

A biopsy of the corresponding tissue is obtained under sterile conditions using standards methods adapted to the specific cell that will be collected. The cells are used extemporaneously or optionally after ex-vivo culture and cell proliferation as follow.

b) Ex-Vivo Culture and Cell Proliferation

Cells used for the preparation of cell compositions according to the invention, such as keratinocytes, bone marrow cells, fibroblasts; periosteum or corneal cells, such as corneal limbal stem cells; melanocytes and Langerhans cell; fat cells; muscle cells such as myoblasts and satellite cells; osteoblasts; chondrocytes; umbilical cord cells; Schwann cells, tendon or pancreatic cells are expanded in a cell carrier medium (e.g. DMEM or Ham's) on plates (e.g. Petri dishes or culture flask) coated with a platelet concentrate according to the invention, preferably autologous, enriched with fibronectin. The culture media may be enriched preferably with DMEM for example in the case of keratinocytes. For cells such as bone osteoblasts, chondrocytes and myoblasts, enzymatic digestion of the corresponding tissue in presence of for example collagenase or trypsin is necessary before plating. Incubation on the plates is performed at 37° C. under a gas flow of 95% oxygen or air and 5% carbon dioxide. Typically, incubation time vary from 10 to 20 min. The cell expansion may be increased (like for example in the case of myoblast, fibroblast and chondrocyte cells) by phototherapy (e.g. light exposure at 633 nm of about 10 min at 2 J/cm$^2$, once a week during the incubation phase).

The explants may be cultured in Petri dishes or culture flask using air-lifting technique (Molnar et al., 1996, *Tissue & Cell*, 28:547-556) and air interface method (Meller et al., 2002, *Br. J Opht.*, 86, 463-471) with half of the explant exposed to air. The culture medium is changed regularly during incubation, such as every 3 days. The expansion of the cells in a 2D mode as planar monolayers, is obtained for example for myoblast, fibroblast and chondrocyte cells. A 3D cell growing pattern can be obtained for example for corneal, myoblast, fibroblast, chondrocyte, adipocyte and keratinocyte cells, by adding diluted autologous platelet concentrate composition according to the invention at about 5 to about 40% volume of plasma or enriched plasma to the culture medium. Typically, the addition of diluted autologous platelet concentrate composition according to the invention is performed 2 or three times during the incubation time. The 3D biological scaffold then obtained allows to enhance the extra-cellular matrix which is useful for autologous stem cell transfer.

After incubation, cells are then released from dishes with gentle trypsin digestion that lifts off the cells and allows them to be pelleted.

c) Cell Quality and Safety Check

The cell viability in the so-obtained cell preparation is checked by microscopic cell count, flow-cytometer cell count together with immunochemistry on tissue markers by standard techniques. Cell viability is also tested via trypan-blue just after cell release by trypsin. Safety of the preparation is also checked through contamination check via microbiology assay to exclude contamination with viruses or bacteria and to avoid transfer of zoonotic infections. The use of FCS is avoided thus preventing transmission of Mad Cow Disease.

d) Administration of the Cell Preparation

The cell preparation obtained above is placed in autologous platelet concentrate composition according to the invention as cell carrier vehicle for transport before delivery to the patient. Then, the cell preparation obtained above is injected or transplanted into the patient. The injection or transplantation mode has to be adapted to the type of cells contained in the cell preparation according to the invention and to the aimed therapeutic or aesthetic effect. More details are given in the Examples below on the method for the preparation and use of the cell compositions according to the invention more specifically, depending on the type of cells and aimed therapeutic or aesthetic effect.

Keratinocyte cell or fibroblast cell preparations according to the invention may be used readily after collection or after cell culture as described above. However, the cell preparations according to the invention are preferably prepared after cell culture as described above.

The cell preparations according to the invention present a better viability and stability (including integrity of cell properties preserved such as ability the synthesize proteins and deliver growths factors) than cells prepared in a medium without autologous platelet concentrate composition according to the invention. Further, cell proliferation so obtained is enhanced: cells grow faster (about 3 to 5 days quicker) and are denser compared to control mediums and serum starved media. The advantage of the process for the preparation of a cell composition according to the invention is that the same autologous medium is used as vector for cell culture, cell preservation, cell injection, vector for cell bio-stimulation and tissue regeneration.

Example 1

Preparation of an Autologous Platelet Concentrate

Separator tubes of the invention are beforehand tested for the good tolerability, the non-toxicity and the non-mutagenicity of the thixotropic gel according to norms ISO 10993-11, ISO 10993-10, ISO 10993-12 and ISO 10993-3.

About 8.5 to about 10-mL of human blood sample are collected within the separator tube of the invention, where the blood is aspirated by the vacuum. The mixture is then centrifuged at approximately 3'800 rpm for about 3.5 min. The platelet-rich plasma is then collected.

The analysis of the platelet concentrate obtained by the method of the invention has shown that it contains 2 to 4 times the normal levels of platelets and growth factors, compared to a natural blood clot, while maintaining normal levels of fibrin and fibrinogen and containing practically no blood cells (<1% hematocrit, compared to 35-50% in a normal blood clot and 15-20% in platelet-rich plasma obtained from known methods of preparation). The study shows also the presence of leukocytes glycoprotein fibronectin and this demonstrates that the coagulating properties are preserved.

The composition of the platelet concentrate (also called RegenPRP™ from Regen Lab, Switzerland) compared to whole blood, whole plasma and platelet-poor plasma is presented in table 1 below:

TABLE 1

| Sample | White Blood Cells ($\times 10^9$/L) | Red Blood Cells ($\times 10^{12}$/L) | Hemoglobin (g/dL) | Platelets ($\times 10^9$/L) |
|---|---|---|---|---|
| Complete blood | 6.6 | 4.43 | 13.5 | 269 |
| Complete plasma | 2.8 | 0.04 | 0.4 | 305 |
| Platelet-rich plasma | 14.2 | 0.57 | 2.1 | 570 |
| Platelet-poor plasma | 0 | 0 | 0.1 | 116 |

The experiment was repeated on several patients and it was observed that the obtained platelet concentrates present reproducible concentrations for platelets (at least $300 \times 10^9$ cells/L), white blood cells (at least $7.0 \times 10^9$ cells/L), fibrinogen (at least 3 mg/L) and erythrocytes (less than $0.6 \times 10^{12}$ cells/L).

The platelet yield obtained by such the method of the invention has been measured (90-99%) and shows to be drastically increased in comparison with the platelet yields (30-62%) obtained from known methods of preparation described in Marx et al., 2004, above.

In addition, it has been shown through ELISA kits (R&D Systems, Inc.) and the response to coagulation activation of the platelet concentrate of the invention, that the activity of coagulation factors is preserved: the concentration of D-dimers (fibrin breakdown products), known markers of coagulation activation, and the lysis process are stable and therefore the coagulation properties of the platelet concentrate are not weakened by the process of the invention.

The levels of growth factors (PDGF, EGF, TGF-β and VEGF) from the platelet concentrate of the invention are demonstrably stable for a period of at least 72 hours (4 days) when stored at room temperature in the sterile separator tube of the invention. The evolution of growth factors PDGF BB, EGF and VEGF over 72 hours is presented on FIG. 1.

The properties of the platelet concentrate according to the invention make it possible to envisage preparing platelet concentrate obtained using the invention's procedure, one to several days before a reparative surgery, in order to reduce the workload in the operating room and speed-up the surgical procedure.

For subsequent therapeutic use, the autologous platelet concentrate is generally mixed with a conventional coagulation activator such as a thrombin activator (e.g. calcium chloride pour example at 10%), optionally mixed with a fibrinogen activator such as thrombin, preferably homologous (e.g. 10 UI to 100 IU per mL of plasma), batroxobin (e.g. 20 BU per mL of plasma) or a thrombin enriched preparation.

Example 2

Therapeutic Use of the Autologous Platelet Concentrate of the Invention a) Patients:

Three patients presenting chronic unhealing wounds are selected:

One 88-year-old patient (Patient 1) suffering from multiple locations Kaposi's angiosarcoma on lower limbs and from a radio-induced necrosis on the left leg. The radio-induced necrosis was resulting from radiotherapy treatment. After 12 months after the end of the low-voltage X-ray treatment, the necrosis was consisting in a deep superinfected ulcer surrounded by a scab (35×25 mm). The wound had been previously unsuccessfully treated with various treatments such as with steroids and healing creams.

One 81-year-old patient (Patient 2) suffering from a vertex spinocellular carcinoma was presenting a cutaneous ulceration (about 10 mm diameter) with peripheral dyskeratosis without any infection sign resulting from a biopsy-resection and a post-surgical radiotherapy (total close of 52 Gy).

One 60-year-old patient (Patient 3) having received a pre-surgical irradiation (7 Gy) for tibia and fibula synostosis on the right leg was presenting a radio-induced necrosis consisting in a deep ulcer (50×30 mm diameter) without inflammation.

b) Treatment:

8.5 mL of blood sample is taken from each patient and centrifuged in a separator tube as described in Example 1, according to the protocol as described in Example 2. The resulting platelet concentrates are then mixed with calcium chloride at 10% vol. Each autologous platelet concentrate composition is then applied on the radio epidermitis wound site of the corresponding patient. The wound is then covered and protected with humid compresses (Day 1).

Between days 3 and 5, the wound status is checked and the wound dressing is changed. At day 7±1, a new application of a new autologous platelet concentrate preparation of the invention is performed. If needed, the same treatment sequence is followed with the same time intervals till the complete cicatrisation of the wound.

c) Healing Effects:

Patient 1: Slow and regular healing of the ulcer. Complete cicatrisation after 189 days.

Patient 2: Very quick healing obtained in 21 days.

Patient 3: Progressive and regular healing. Complete cicatrisation after 41 days.

These results show the benefit effect of the platelet concentrate composition of the invention in the healing of chronic radio-induced ulcers, even in the case of those which were resistant to previous topic treatments and in the absence of any allergic reaction.

Example 3

Therapeutic Use of the Autologous Platelet Concentrate of the Invention in Combination with an Autologous Thrombin Enriched Serum To activate coagulation, an alternative to the mixture of the platelet concentrate of the invention with a thrombin activator before the use on a patient, as described in Example 1, is the combination of the platelet concentrate of the invention with a fibrinogen activator such as a thrombin enriched composition and preferably with a thrombin serum (e.g. autologous) according to the invention.

a) Preparation of an Autologous Thrombin Serum (ATS)

An autologous thrombin serum to be used as a thrombin enriched preparation in the context of the invention is prepared by a process which comprises the addition to a patient's whole blood sample (e.g. 8 mL) collected in a separator tube of the invention as described in Example 1, a 95% v. ethanol solution (e.g. 1 mL) and calcium chloride 10% (e.g. 1 mL). The mixture (also called RegenATS™ from Regen Lab, Switzerland) is then allowed to precipitate for about 30 min at room temperature.

After 30 min, almost 80% of the anti-thrombin (among other proteins like fibrinogen) is precipitated; then the tube is centrifuged at or about 1'500 g for about 8 to 10 min and the autologous thrombin serum is ready for use in combination with the platelet-rich concentrate of the invention.

b) Combined Preparations

One of the originality of this process is that after the initial step of incubation of the autologous thrombin serum preparation process (e.g. at least about 30 min), the separator tubes of the invention containing respectively the autologous thrombin serum preparation and the platelet concentrate preparation can be centrifuged simultaneously in order to get the two blood extract preparations ready for use at the same time.

c) Combined Use

To allow the polymerization of fibrinogen into a fibrin mesh (which occurs during the coagulation process) to occur only at the moment of application of the platelet-rich preparation on the wound, the platelet concentrate composition and autologous thrombin serum (coagulation activator) are applied simultaneously at a vol. ratio of about 10:1 to about 10:3 (concentrate to coagulation activator ratio) to the wound.

The simultaneous delivery of both preparations is achieved for example by a device comprising two syringes (e.g. 10-mL syringe for the platelet concentrate composition and a 1-mL or 3 mL syringe for the thrombin serum), that releases the preparations simultaneously so that they mix and polymerize upon contact with the wound.

Example 4

Therapeutic Use of the Autologous Platelet Concentrate of the Invention in Combination with Skin Cell Extract A total of 35 patients having received a skin graft (representing less than 15% of the skin surface) have been included in the study. Patients treated with immunosuppressants or corticoids or with renal insufficiency or severe peripheral artheropathy were excluded.

All the following manipulations are performed under the strict rules of asepsy and sterility.
Group A: 13 Patients
a) Preparation of Platelet Concentrate A 8.5 mL sample of whole blood from each patient (from a higher limb where no perfusion is present) is collected in a separator tube according to the invention. The separator tube with the whole blood is immediately centrifuged during about 8 min at 2'800 rpm. Before the enriched plasma (PRP) is collected, the operator discards the half or 2 mL of the supernatant and then re-suspends the platelets in the remaining plasma. The platelet-rich concentrate is then transferred to a sterile tube maintained at a temperature of 37° C.
b) Wound Coating The autologous platelet concentrate of the invention (also called RegenPRP™) is mixed with a solution of calcium chloride 10% in a ratio 10:1 and the graft donor site (where skin was removed) of each corresponding patient is coated with the autologous corresponding mixture in order to obtain coagulation of the platelet concentrate on the wound.
Group B: 8 Patients
a) Skin Cell Sampling on the Patient Keratinocytes are extracted from each of the patients from this group. A thin healthy skin sample (about 2 cm$^2$) is removed from each patient and washed three times in a PBS solution. The washed biopsy is then deposited in a Petri dish containing trypsin and cut into very small fragments (0.5 cm*0.5 cm) with a scalpel. The skin fragments are then incubated during 45 min at 37° C. on a stirring device in 20% volume of autologous platelet concentrate composition according to the invention, also called RegenPRP™, obtained above. The supernatant is then collected, centrifuged and cells are re-suspended in a PBS solution. The keratinocytes count is determined under microscope. Finally, the obtained keratinocytes were re-suspended in the autologous platelet concentrate according to the invention (5-40% vol.) from the corresponding patient.
b) Preparation of Platelet Concentrate The procedure is the same as for Group A:
c) Wound Coating The keratinocyte suspension (also called RegenExtracell™) is applied as soon as ready (the entire preparation not exceeding a day) on the wound on the same way as described in the case of Group A.
Control Group: 14 Patients The graft donor site of each patient of this group is coated with a non-therapeutic compress (Jelonet®).
Randomization and Treatment In the surgery bloc, after the graft skin removal, the donor site is coated with a temporary compress soaked with an adrenaline solution (1 ampoule of 1 mg/mL of adrenaline diluted in 500 mL NaCl 0.9%) and depending on the randomization table, the donor site is treated according to the three following methods:

Groups 1 and 2: Coating of the wound with the respective wound healing composition and covering of the wound with a non-therapeutic compress (Jelonet®).

Group 3: Direct covering of the wound with a non-therapeutic compress (Jelonet®).

The compresses are then covered with Kerlix® bands and elastic bands such as "Velpeau".
Treatment Efficacy Criteria The efficacy of the treatment is evaluated according to 3 criteria:

The time needed for the complete cicatrisation of the treated site (healing time or HT in days)

The epitheliazation (evolution of the cicatrisation progress) measured at day 5 after the treatment according to 7 degrees:
0: Absent
1: Slight
2: Moderate
3: Important
4-7: Very important, increasing degrees of importance;

The pain evaluated at day 5 after the treatment by the patient him/herself, generally at the time of compress change on a scale from 0 to 10 (0: no pain and 10: extreme pain).

The compress is opened at day 5 post-surgery to allow the evaluation of the quality of the treatment and covered with new Jelonet® compresses covered with dry compresses.

Figure 2:
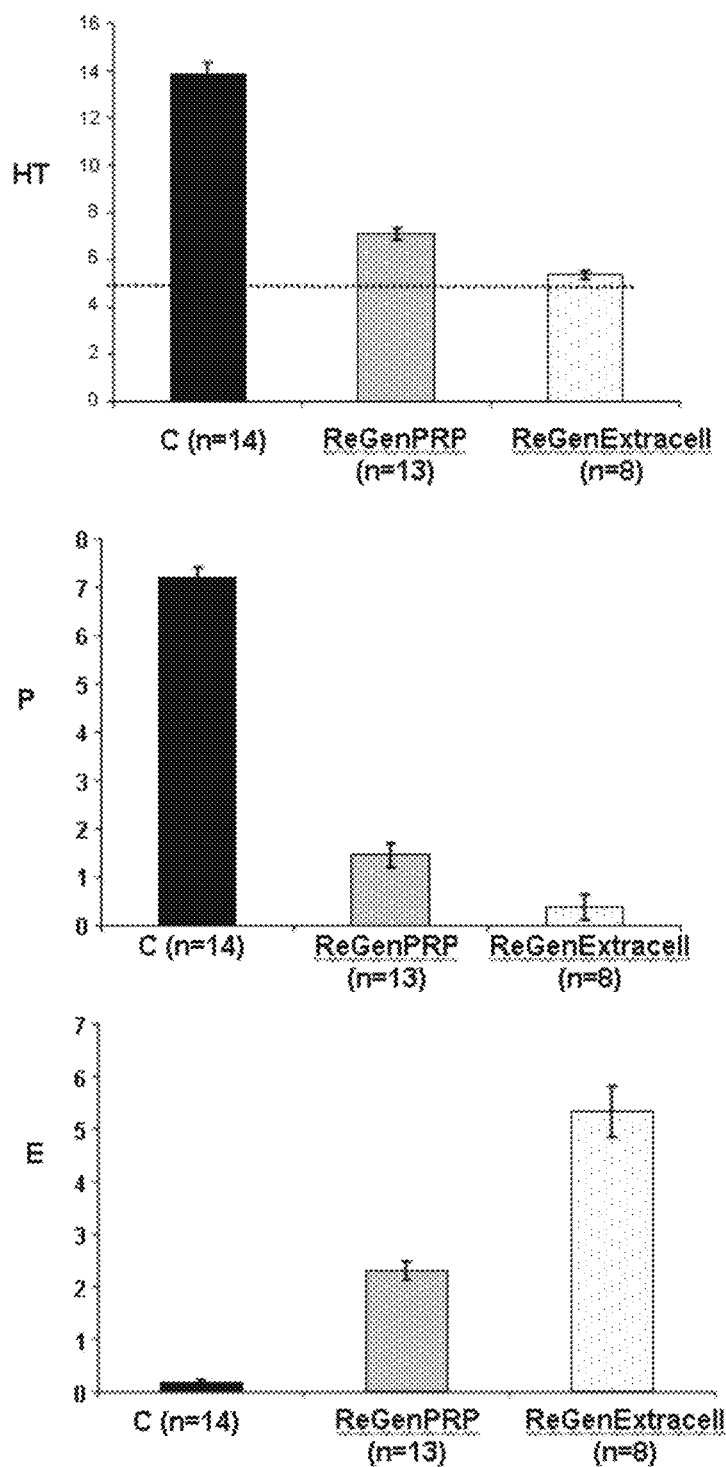
FIG. 2 is a schematic representation of the outcome of the treatment of a skin graft donor site with a preparation containing a platelet concentrate composition according to the invention in comparison with a control group in terms of healing time in days (HT), pain at day 5 on a scale 0 to 10 (P) and epithelization at day 5 on a scale 0 to 7 (E). Control group: C, platelet-rich preparation alone: RegenPRP™, platelet-rich preparation and autologous keratinocytes: RegenExtracell™. The dotted line indicates when the first bandage is changed at day 5.

The compress is then changed very two days till the complete cicatrisation. Any side effects or medical complications are watched during the whole duration of the cicatrisation process.
Results The results of the treatments for each patient group (Control group: C, Group A: RegenPRP™, Group B: RegenExtracell™) are presented on FIG. 2 in terms of healing time in days (HT), pain at day 5 (P) and epitheliazation at day 5 (E). The dotted line indicates when the first bandage is changed at day 5.

The cicatrisation process is clearly stimulated by the use of the platelet concentrate of the invention as compared to the control group. The quality of the cicatrisation is also better in the case of the use of platelet concentrate of the invention. In addition, the pain at the donor site is dramatically reduced in the case where the platelet concentrate of the invention was used as compared to the control group.

All the beneficial effects of the platelet concentrate of the invention are increased when a mixture of keratinocytes suspended in the platelet concentrate of the invention is used.

The mean healing time is of 7 days for the group treated with a platelet concentrate of the invention and 5 days when keratinocytes are suspended in the platelet concentrate as compared to an average of 12 days in the control group.

Tolerability was excellent and no side effect or allergy has been detected.

This shows that the platelet concentrate of the invention alone or combined with keratinocytes is very efficient in accelerating the wound healing process and not only decreases the pain, but also the inflammatory reaction and improves the final aspect of the scar.

Alternatively, using the same process of dissociation, skin cells can be placed in a Petri dish coated with the autologous platelet concentrate composition according to the invention, also called RegenPRP™, obtained above and cultured for 2 to 5 days. Then, before the graft, the obtained skin cell preparation may be sprayed onto the wound, in order to prepare the site for a better bio integration of the implanted cells, and a better expansion in vivo.

Example 5

Cosmetic Use of the Autologous Platelet Concentrate of the Invention

An autologous platelet concentrate composition is prepared as described in Example 1.5 mL of this platelet concentrate composition (also called RegenACR™: (Autologous Cell Rejuvenation) from RegenLab, Switzerland) is injected subcutaneously in a wrinkle groove as wrinkle filling material, in the same way as commonly done with other wrinkle filler such as hyaluronic acid. The deepness of the wrinkle is progressively decreasing within the first weeks after the treatment and at the site of injection, a very clear regeneration of the area is obtained with an optimal result at two to three months. As opposed to what observed with other wrinkle filling materials, neither inflammation, nor swelling is observed at the site of injection and the benefit is durable as opposed to hyaluronic acid which is bio-resorbed after 4 to 6 months.

Known methods to study the effect autologous platelet concentrate compositions of the invention on wrinkle deepness can be used to such as a three-dimensional reconstitution of skin relief by optical profilometry (stylus method) (Grove et al., 1989, *J. Am. Acad. Dermatol.*, 21:631-7) or by laser microscopy on silicon skin replicas. Another method consists in the in vivo quantification of the skin surface "Surface evaluation of living skin" or "SELS" through the analysis of images in UV light (Tronnier et 1997, *Akt. Dermatol.*, 23:290-295). Another method for the surface evaluation of living skin is based on an optical system with a CCD camera measuring the four skin parameters: roughness, scaling, smoothing and wrinkling (Fluhr et al., 1995, *Akt. Dermatol.*, 21:151-156). Dep dermal augmentation can be assessed by ultrasound, Dermascan®, Denmark).

Other examples of cosmetic use of the autologous platelet concentrate of the present invention include:

Admixing the platelet concentrate according to the invention with a cream, preferably an emulsion, before application to a wound, after surgery or on healthy skin. During the absorption process, the platelet preparation is carried into the skin by the cream or emulsion in order to amplify the hydrating benefit and to bio-stimulate the regeneration or rejuvenation of the skin.

Using a hydrogel like the Albugel (EP 1 543 846) preparation of 100% Albumin or any other hydrogel resulting from the reticulation of Albumin and other chemical compound like polyethylene glycol or any other ingredient, using a paper based highly hydrophilic, a carrier to leave in contact with the skin until the platelet rich plasma is absorbed.

Example 6

Autologous Muscle Cell Association Preparation

Example of autologous cell association according to the invention can be prepared by using the process according to the invention wherein skeletal muscle cells (muscle progenitor cells or satellite stem cells) are provided under step (d) or (e).

a) Myoblast Progenitor Stem Cells

Skeletal muscle biopsy is obtained from the Vastus lateralis and measures 7×3 cm. Muscle is primed the day before biopsy, with intra-muscular injection at proposed biopsy site (10 by 15 cm skin area on lateral aspect of thigh overlying the vastus lateralis muscle and just above the knee joint, on either side) with Decadon and Marcaine (long acting Lignocaine). Muscle is diced and enzymatically digested with combination of collagenase, pronase and trypsin (Worthington). Enzyme action is neutralised using patients serum in DMEM culture medium. Muscle explants are plated Petri dishes coated with the autologous platelet concentrate composition according to the invention, also called RegenPRP™ (prepared as described in Example 4) and incubated in 95% oxygen and 5% carbon dioxide at 37° C. for 3 to 4 weeks. Desmin or CD-56 expression is used as myoblast marker to identify myoblasts from fibroblasts. Myoblast progenitor cell proliferation in 3D is shown on FIG. 3.

Cell proliferation can be enhanced by photo-light exposure at 633 nm of 2 J/square centimetre for 10 min during culture. The day of transplantation (e.g. after 3 to 4 weeks of incubation), the skeletal muscle cells are released are released by trypsin and placed in the autologous platelet concentrate composition according to the invention, also called RegenPRP™ (prepared as described in Example 4). Injections into the myocardium can be made as direct injection or multiple catheter injections into the left ventricle myocardium. The myoblast cell preparation according to the invention is useful for cardiac disorders such as heart regeneration, treatment of heart failure, chronic cardiac failure, ischemic and non-ischemic cardiac failure and non-ischemic cardiomyopathy. Ejection fraction can be improved by 9% for cardiac recipients of skeletal myoblasts.

The above cell preparation may also be useful for in the treatment of urinary incontinence (myoblast cell extracts prepared as described above and injected into the bladder neck), reflux oesophagitis or gastro-oesophageal reflux disorder (myoblast cell extracts prepared as described above injected into the lower oesophageal sphincter) and anal incontinence (myoblast cell extracts prepared as described above and injected in para-anal area).

Alternatively, a combined preparation of fibroblast and myoblast may be carried out (fibroblasts are present in the muscle biopsy and sprout from the perimysium alongside the myotubes and satellite stem cells).

In case of the treatment of cardiac disorders, a mix of fibroblast cell preparation and myoblast cell preparation (obtained as indicated above) is inserted into the myocardium in a ratio fibroblast/myoblast of about 30:70.

For bladder neck incontinence treatment, a separate culture of fibroblasts is made at the same time as the myoblasts as described above and the fibroblast cell preparation is injected para-urethrally and myoblast cell preparation is injected into the rhabdosphincter, under ultrasound control.

b) Satellite Stem Cells

Myoblasts and satellite stem cells are cultured ex vivi in presence of autologous platelet concentrate composition according to the invention, also called RegenPRP™. Cell proliferation priming is observed after 7-days of primary culture.

Cells are then harvested after incubation of about: 3-4 weeks and placed in tissue culture medium (DMEM plus 5-10% vol. autologous platelet concentrate composition according to the invention) containing a human de-epithelialized amnion patch measuring 4×4 cm and the autologous platelet concentrate composition according to the invention, also called RegenPRP™ (prepared as described in Example 4). The preparation is then subjected to UV irradiation for 10 min. During incubation (typically about 2 to about 3 weeks), the cells spread over the amnion construct and form a monolayer. Viability and monolayer progress is assessed by twice weekly biopsy of patch edge and histological assessment for thickness of monolayer.

The day of transplantation (e.g. after about 3 to 4 weeks of incubation), the ventricular surface is spread with the autologous platelet concentrate composition according to the invention, also called RegenPRP™ (prepared as described in Example 4) and then the patch obtained above is placed with cells down side onto a raw surface of the ischemic ventricle in order to allow the stem cells on the patch to populate the ischemic segment after ventricular injection. Cell retention is maintained by the amnion that is inert and induces no immunological reaction.

The satellite stem cell preparation according to the invention is useful for heart regeneration and treatment of heart failure as tissue engineering preparation for cardio myoplasty.

Example 7

Autologous Fibroblast Cell Association Preparation

Example of autologous fibroblast cell association according to the invention can be prepared by using the process according to the invention wherein dermal fibroblast cells are provided under step (d) or (e).

Figure 3:
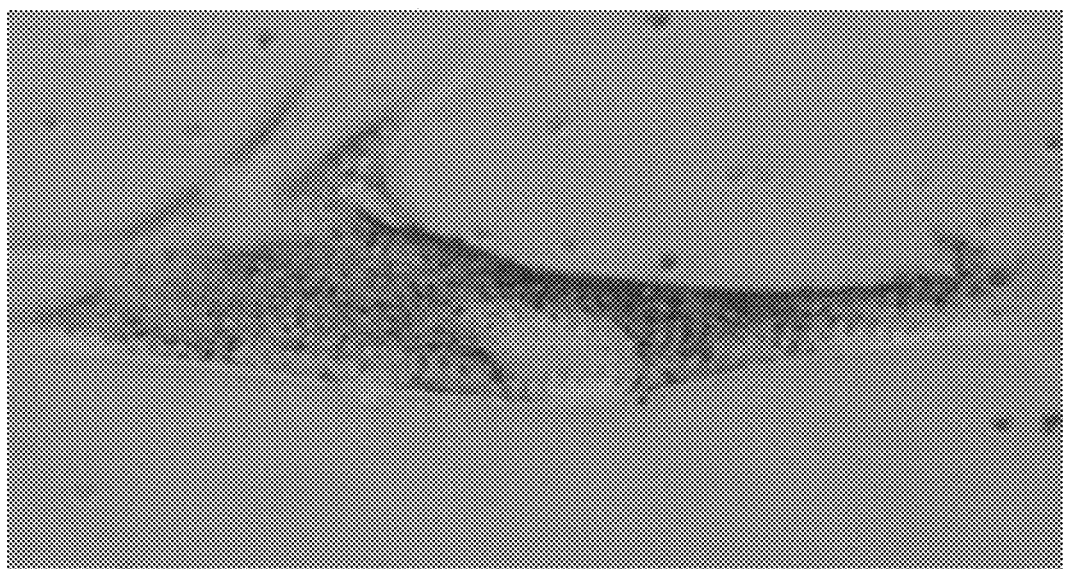
FIG. 3 represents the morphology of a human fibroblast expanded in cell preparation according to the invention under the condition described in Example 7, showing branching and filopodia×5'000 (Olympus® inverted microscope).
Figure 4A:
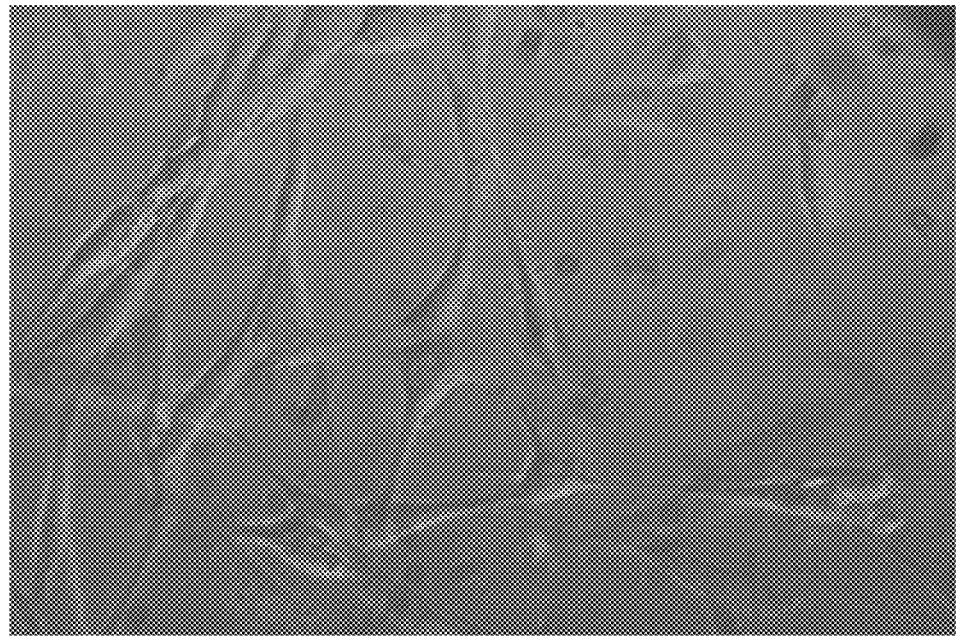
FIG. 4a represents a 3D scaffold of human fibroblasts from a cell preparation according to the invention under the condition described in Example 7.
Figure 4B:
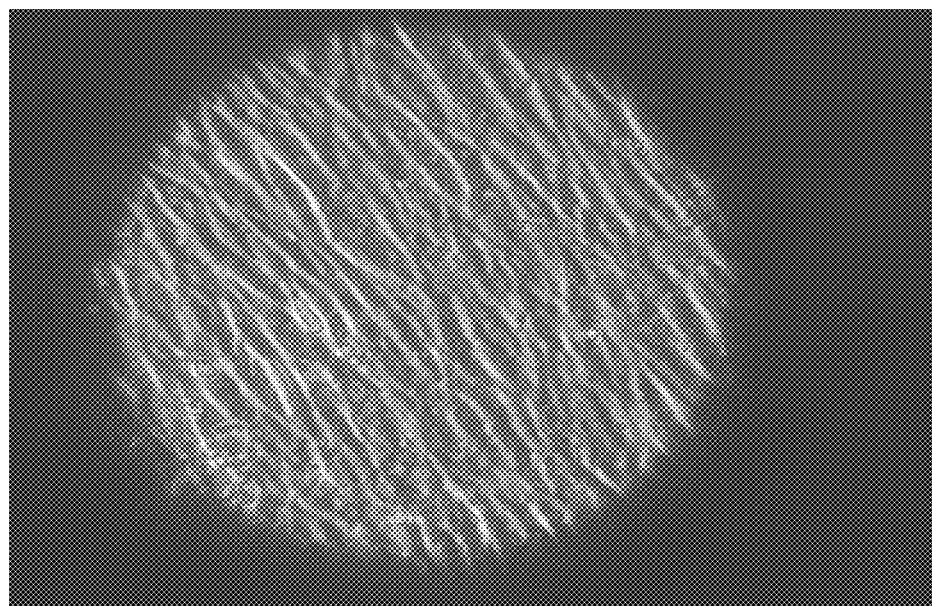
FIG. 4b represents monolayers of fibroblasts densely packed in 3D culture from a cell preparation according to the invention under the condition described in Example 7.

Dermal fibroblasts are isolated and expanded according to the following procedure:

One month before biopsy, the prime donor skin area (behind an ear of anterior axillary fold, e.g. non solar aged area) is treated with vitamin A cream to activate the dermal fibroblasts. A skin biopsy of 10×6 mm full thickness is performed and dissected under microscope to remove all epithelium. The epithelialize biopsy (dermis) is then cut into 3×3 mm blocks as explants. The papillary dermis is then placed upwards and cultured using air-lifting technique (Molnar et al., 1996, above) and air interface (Meller et al., 2002, above) with half of the explant exposed to air. The explants are plated (e.g. 6 explants per well) in DMEM and cultured at 37° C. at 95% oxygen and 5% $CO_2$ for about 3-5 up to about 9 days in Petri dishes or culture flask. The medium is changed every 3 day. The fibroblasts expansion in 2D mode as planar monolayers, as static growth is observed during incubation. At days 7 to 9 after the start of incubation, a change in proliferation and phenotype pattern to 3D is obtained by adding diluted 5-10% autologous platelet concentrate composition according to the invention, also called RegenPRP™ (prepared as described in Example 4) to the culture medium: cells are primed with RegenPRP™ (0.2 ml per well) just to cover base. Cells grow then as a 3D fibrin gel matrix (FIG. 3). Cells then differentiate to form biological scaffold or network in fibrin gel such as shown on FIGS. 4a and 4b. Cell number is measured by daily counting under a grid and to assess apoptosis: use inverted microscope (Olympus®).

After 3 to 6 weeks of incubation, the cells are harvested from the fibrin gel. Cell viability is assayed with classical Trypan blue method and with bacteriological evaluation, including virus contamination.

The expanded fibroblast cell extract obtained above is placed in a syringe in presence of autologous platelet concentrate composition according to the invention, also called RegenPRP™ and the preparation is injected into face wrinkles, more specifically under the wrinkles. Injections must be performed over the whole face to cover forehead, jowls, molar region, cheeks, chin and neck.

Cell expansion may be increased by photo light exposure of cell culture at 633 nm. The fibroblast cell preparation according to the invention is useful for facial rejuvenation, amelioration of facial wrinkles and rhytids, treatment of skins damaged by radiations (radiodermatitis or sun damaged skin), aged skins or burned skins and/or in the amelioration of facial wrinkles, rhytids, acne (especially after dermabrasion treatment), burns, rubella or small pox scars, vitiligo, lipoatrophy or lypodystrophy, such as AIDS-related lypodystrophy; Kaposi's sarcoma, skin keloids or Dupuytren's palmar fibromatosis and/or in skin rejuvenation treatments.

Example 8

Autologous Fat Cell Association Preparation

Example of autologous cell association according to the invention can be prepared by using the process according to the invention wherein adipose stem cells are provided under step (d) or (e).

Adult adipose stem cells are isolated by standard culture method in 5-10% vol. an autologous platelet concentrate composition according to the invention, also called RegenPRP™. The preparation is then injected with an applicator into patients suffering from tissue deficiencies, such as post traumatic deficiencies or aged-related deficiencies for patients being around about 40 years-old.

The fat cell preparation according to the invention is useful for the treatment of lipoatrophy such as in HIV/AIDS patients and others congenital hemiatrophy of the face.

Example 9

Autologous Chondrocyte Cell Association Preparation

Example of autologous cell association according to the invention can be prepared by using the process according to the invention wherein chondrocyte cells are provided under step (d) or (e).

Cartilage is isolated from the donor's knee (biopsy size 10×5 mm) and diced. The cartilage chondrocyte cells are cultured for 4-6 weeks in medium enriched with an autologous platelet concentrate composition according to the invention, also called RegenPRP™, Cartilage cells are then released by enzymatic digestion (collagenase and pronase). The cell preparation is then incorporated surgically into the patient with deep chondral defects and damage.

The chondrocyte cell preparation according to the invention is useful for the treatment of deep cartilage damage and erosion or arthroscopy.

Another example of the use of a chondrocyte cell preparation according to the invention is the use in rhinoplasty without surgery by a single injection procedure: A patient suffering from congenital cartilage nose atrophy.

The day before injection, a biopsy of the cartilage of the ear 0.4*0.4 cm is performed and placed in a sterile recipient filled with DMEM and antibiotic. The biopsy is treated with enzymatic digestion including trypsin and collagenase. The released chondrocytes are then re-suspended in the autologous platelet concentrate composition according to the invention where 10% $CaCl_2$ have been added.

The patient receives first a local anesthesia, and nose disinfection. Then, the above chondrocyte preparation is injected on the cartilage surface and or periosteum membrane of the site requiring augmentation of volume or lift. In a second phase, autologous platelet concentrate composition according to the invention where 10% $CaCl_2$ have been added is injected into the superficial part of the nose skin, in order to biostimulate regeneration and the rejuvenation of the skin. After one hour, the injection is achieved and the patient could return home. An exceptional recovery of viable cells is observed: the amount of chondrocyte cells and plasma cells recovered and injected was about $10^9$ cells.

The chondrocyte cell preparation according to the invention is therefore useful for the treatment of nasal cartilage defects, without surgical procedure, but only by injection.

Example 10

Autologous Umbilical Cord Stem Cell Association Preparation

Example of autologous cell association according to the invention can be prepared by using the process according to the invention wherein umbilical cord stem cells are provided under step (d) or (e). Umbilical cord stem cells are isolated and then cryo-preserved and used to treat blood disorders.

The umbilical cord stem cell preparation according to the invention is useful for the treatment of haematological diseases (like Thalassaemia).

Example 11

Autologous Tendon Cell Association Preparation

Example of autologous cell association according to the invention can be prepared by using the process according to the invention wherein tendon cells are provided under step (d) or (e).

Tendon fibroblast cells are isolated according to procedure standard procedures in 5-10% vol. of autologous platelet concentrate composition according, to the invention. The tendon fibroblast cells are cultured for about 1 to about 3 weeks in culture medium enriched with an autologous platelet concentrate composition according to the invention, also called RegenPRP™. The cell preparation is then injected into the patient at the injury site (e.g. tendon torn, arthritic area). The injection can be guided by echography, for localisation of the damaged site, and better graft of the implanted solution.

The injection of the tendon fibroblast cell preparation may also be performed next to rotator cuff in shoulder: first the rotator cuff tear is repaired arthroscopically, then the tendon fibroblast cell preparation is injected via a long catheter onto the sutured area. This improves the healing of the tendon fibroblast at the edge of the rotator cuff, prevents haematoma in confined space under the acromion, prevents frozen shoulder by speeding up healing and enhancing rehabilitation and, joint movement.

The tendon cell preparation according to the invention is useful for the treatment of tendons torn, arthritis in joint caused by traumas or by aging, rotator cuff in shoulder.

Example 12

Autologous Ligament and Gingival Cell Association Preparation

Example of autologous cell association according to the invention can be prepared by using the process according to the invention wherein periosteal membrane and gingival cells are provided under step (d) or (e).

Under general and local anesthesia, periosteum (approximately 10×10 mm) is aseptically harvested from the buccal side of the mandibular body in four healthy female beagle dogs. The harvested periosteum is cut into 3×3 mm pieces. The tissues are placed directly on a 6-well plate and cultured (for about 3 to about 6 weeks) in a humidified atmosphere of 5% $CO_2$ and 95% air at 37° C. in a culture medium enriched with an autologous platelet concentrate composition according to the invention, also called RegenPRP™. The periosteal membrane and gingival cells are isolated by enzymatic digestion and cultured by static technique.

Typically, 6 weeks of culture was sufficient to obtain appropriate periosteal membrane thickness for grafting.

Patients are separated into two groups: (1) a control group which receives an autologous platelet concentrate composition according to the invention without periosteal membrane cells and (2) a treatment group which receives the periosteum membrane cell preparation obtained above. The autologous platelet concentrate composition (in control group) and the cell preparation (for the treated group) are respectively injected into the patient at the injury site.

12 weeks after operation, the periosteal membrane cell preparation had completely disappeared in both control and treatment group. Bone regeneration in the treatment group with cultured periosteum membrane was significantly greater than that in the control group: the thread of dental implants was almost covered with the regenerated bone, while most of the thread in the control group was exposed. The treatment group demonstrated relatively thick and dense lamellar bone formation from bottom to top of the created defect. Thick layers of woven bone were attached to the implant surface and osteoblast like cells were observed around the surface. Although abundant neovascularization was observed in the bone matrix, inflammatory cells were rarely observed. The border between the regenerated and original bone was not clear. In the control group, specimen exhibited thin cortical bone formation at the dehiscence defect. Scarce woven bone was observed between the implant surface and the cortical bone, and few osteocytes and osteoclasts were observed within the bone matrix and at the surface, respectively. Bone density was significantly higher in the treatment group than the control group. The mean LF values were 77.58±1.14% and 37.03±4.63% in the treatment and control groups, respectively (P<0.05).

The periosteal membrane and gingival cell preparation according to the invention is useful for the treatment of periodontal disease and dry sockets, especially in promoting bone regeneration at sites of implant dehiscence.

Example 13

Autologous Corneal Cell Association Preparation

Example of autologous cell association according to the invention can be prepared by using the process according to the invention wherein corneal cells are provided under step (d) or (e).

A biopsy is taken from the epicanthis on the edge of the cornea and the corneal limbal stem cells were expanded for autologous transplantation in the same person after 4 weeks of culture in Petri-dishes or flasks coated with an autologous platelet concentrate composition according to the invention, also called RegenPRP™.

The corneal corneal cultured stem cells (of limbal origin) may be ex vivo engineered onto the surface of de-epithelialised human amnion in a monolayer, after seeding the construct with a suspension of cultured and viable corneal keratinocytes according to the invention. About 500,000 cells are used for the seeding and the cells are allowed to cover the surface of the construct with cells after further incubation of about another 3 weeks. The engineering with cells occurs after about three weeks of primary cell culture, and re-seeding may be necessary. The resulting biological cell-biocomposite construct consisting of collagen, amnion fibers and corneal keratinocytes, consisting of membrane and monolayer of cells.

The corneal cell preparation according to the invention can be spread onto a dissolvable contact lens that is applied to the damaged cornea. The contact lens disappears and the cells close the corneal defect.

The corneal cell preparation according to the invention can be administered topically in eye drops in patients suffering from dry eye symptoms. Alternatively, the above amnion can be used on its own on the scarred cornea or the construct and the cell preparation according to the invention can be attached to the inside of a biological or artificial contact lens and then applied to the cornea and covered with an eye pad.

The corneal cell preparation according to the invention is useful in alleviating the pain of dry eye, for the treatment of Steven's Johnson Syndrome and corneal blindness due to acid and corrosive alkali burns in industry, corneal ulcers such as recalcitrant neurotrophic, herpetic and immunologically induced corneal ulceration.

Example 14

Autologous Bone Marrow Cell Association Preparation

Example of autologous cell association according to the invention can be prepared by using the process according to the invention wherein bone marrow cells are provided under step (d) or (e).

Hip bone marrow is harvested and centrifuged in a ready-to-use device for the preparation of a platelet concentrate according to the invention (also called RegenBCT™ (Blood Cell Therapy) of in order to separate red blood cells.

The bone marrow cell preparation is then admixed to the platelet concentrate according to the invention and applied or injected with an applicator with addition of $CaCl_2$ to the injured site of the patients.

The bone marrow cell preparation according to the invention is useful for the treatment of ischemic and non-ischemic cardiac disease, bone defect, cartilage defect.

Example 15

Autologous Schwann Cell Association Preparation

Example of autologous cell association according to the invention can be prepared by using the process according to the invention wherein Schwann cells are provided under step (d) or (e).

Under local anaesthesia, a biopsy is performed either the N. Saphenous of N. SURALIS in the lower extremity. The nerve biopsy is cut into small blocks and primary cultures are induced in Petri dishes enriched an autologous platelet concentrate composition according to the invention, also called RegenPRP™.

Monolayers are expanded in 3D and the cells are eventually harvested by trypsin digestion and concentrated in a syringe for local infiltration of the surgically exposed and damaged spinal cord. The cultivated cells have been shown to contain myelin.

The Schwann cell preparation according to the invention is useful for the treatment of peripheral nerve damage, nerve suture and spinal cord injury.

Example 16

Autologous Human Islet Cell Preparation

Example of autologous cell association according to the invention can be prepared by using the process according to the invention wherein pancreas islet cells are provided under step (d) or (e).

Pancreas islets are harvested by open biopsy and separated by conventional enzymatic digestion and Ficoll or Hypaque separation (Page et al., 2007, Diba. Vas. Dis. Res., 7-12) in a medium enriched with an autologous platelet concentrate composition according to the invention, also called RegenPRP™.

The pancreas islet cell preparation is then injected as a bolus via the portal vein into the liver.

The pancreas islet cell preparation according to the invention is useful for the treatment of type1 diabetes or insulin-dependent diabetes and for the reversal of hyperglycaemia of diabetes mellitus.

Example 17

Autologous Human Osteoblast Cell Preparation

Example of autologous cell association according to the invention can be prepared by using the process according to the invention wherein osteoblast cells are provided under step (d) or (e).

Cortical punch bone biopsy is derived from the iliac crest or equivalent site (maxilla) under local anaesthesia. The bone biopsy is placed aseptically in DMEM medium at 4° C., or equivalent transport medium by those experienced in the art of bone and osteoblast culture ex vivo. The bone biopsy is then diced and digested in diluted 0% type-1 collagenase (Sigma or Boehringer) at 37° C. for 15 min under laminar flow hood. Alternatively, trypsin digestion (Worthington) may be used alternatively. Enzymatic digestion is terminated with three washes with an autologous platelet concentrate composition according to the invention, also called RegenPRP™ at 10% in DMEM at 4° C. The preparation is centrifuged, pelleted and resuspended. The bone fragments are plated on Petri dishes or flasks as explants with air-lifting technology in an autologous platelet concentrate composition according to the invention, also called RegenPRP™. The preparation is cultured at 37° C. with antibiotics, gentamicin and amphotericin-B under a gas flow of 95% air and 5% $CO_2$. The culture medium is changed three times per week, each time spiking DMEM medium with 10% vol. of an autologous platelet concentrate composition according to the invention. The cell viability and morphology are evaluated three times a week to assess cell crawling, apoptosis and 3D dimensional monolayer progression. The formation of microfilament and differentiation is assessed by inverted microscopy (Olympus®). Absence of bacterial and viral contamination is checked. Osteoblasts can be engineered onto human amnion to create cell biocomposite scaffold and cell monolayer carrier/construct after membrane seeding with 100,000 cells as obtained above and allowing monolayer membrane expansion over 3-4 weeks allowing unique construction of osteoblast-amnion-membrane construct for use and transfer to cover a bone defect or grafted area following non-union of fracture in any site.

The osteoblast cell preparation according to the invention is useful for the treatment of bone defects, bone grafts or bone disorders.

The invention claimed is:

1. A sterilized, vacuum sealed separator tube for preparing a therapeutic platelet concentrate from whole blood comprising:
   an inlet adapted to introduce whole blood;
   an anticoagulant; and
   a thixotropic gel;
   wherein, when the separator tube is at least partially filled with the whole blood and centrifuged at a force of about 1,500 g up to about 2,000 g for about 3 to about 10 minutes once in a single centrifugation, blood components in the whole blood are separated into at least: (i) the therapeutic platelet concentrate obtained without supernatant removal and contains greater than about 400 billion platelets per liter; and (ii) red blood cells.

2. The separator tube according to claim 1, wherein the anticoagulant comprises either: (i) a sodium citrate solution; or (ii) a 0.1 M sodium citrate solution.

3. The separator tube according to claim 1, wherein the anticoagulant comprises anhydrous sodium citrate.

4. The separator tube according to claim 1, wherein the thixotropic gel is selected from a polyester-based gel or a polymer mixture gel.

5. The separator tube according to claim 1, wherein the separator tube is comprised at least of polyethylene terephthalate (PET).

6. The separator tube according to claim 1, wherein the therapeutic platelet concentrate has a platelet yield of about 90% to about 99%.

7. The separator tube according to claim 1, wherein the therapeutic platelet concentrate contains fibrinogen at a concentration of at least about 3 mg/L.

8. The separator tube according to claim 1, wherein the therapeutic platelet concentrate contains at least about $2.8 \times 10^9$ white blood cells per liter.

9. The separator tube according to claim 1, wherein the therapeutic platelet concentrate further comprises platelet derived growth factors, (PDGF), vascular endothelial growth factors (VEGF), and epidermal growth factor (EGF) that remain stable for a period of at least 72 hours when stored at room temperature in the separator tube.

10. A method of making a therapeutic platelet concentrate comprising:
   a) providing the sterilized, vacuum-sealed separator tube of claim 1;
   b) introducing whole blood to the separator tube through the inlet;
   c) centrifuging the separator tube containing whole blood in b) at a force of about 1,500 g up to about 2,000 g for about 3 to about 10 minutes only once; and
   d) resuspending and mixing the contents of the separator tube after a single centrifugation,
   wherein after the centrifuging and resuspension/mixing, the whole blood is separated into at least: (i) a therapeutic platelet concentrate containing greater than about 400 billion platelets per liter; and (ii) red blood cells.

11. The method according to claim 10, wherein the anticoagulant comprises a 0.1 M sodium citrate solution.

12. The method according to claim 10, wherein the anticoagulant comprises anhydrous sodium citrate.

13. The method according to claim 10, wherein the thixotropic gel is a polyester-based gel.

14. The method according to claim 10, wherein the separator tube is comprised at least of polyethylene terephthalate (PET).

15. The method according to claim 10, wherein the therapeutic platelet concentrate contains fibrinogen at a concentration of at least about 3 mg/L.

16. The method according to claim 10, wherein the therapeutic platelet concentrate contains at least about $2.8 \times 10^9$ white blood cells per liter.

17. The method according to claim 10, wherein the therapeutic platelet concentrate further comprises platelet derived growth factors, (PDGF), vascular endothelial growth factors (VEGF), and epidermal growth factor (EGF) that remain stable for a period of at least 72 hours when stored at room temperature in the separator tube.

18. The method according to claim 10, wherein the separator tube has a useable vacuum of from about 8 mL to about 10 mL.

19. The method according to claim 10, wherein the separator tube is centrifuged in c) at about 3,800 revolutions per minute (rpm) for about 3.5 minutes.

20. The separator tube according to claim 1, wherein the thixotropic gel is present in an amount of from about 1 mL to about 3 mL.

21. The method according to claim 10, wherein the thixotropic gel is present in an amount of from about 1 mL to about 3 mL.

22. The separator tube according to claim 1, wherein the anticoagulant is present in an amount of about 3.5 mg/mL.

23. The method according to claim 10, wherein the anticoagulant is present in an amount of about 3.5 mg/mL.

24. The separator tube according to claim 1, wherein the thixotropic gel is non-toxic and non-mutagenic.

25. The method according to claim 10, wherein the thixotropic gel is non-toxic and non-mutagenic.

26. A sterilized, vacuum sealed separator tube for preparing a cosmetic or skin repair platelet concentrate from whole blood comprising:
   an inlet adapted to introduce whole blood;
   an anticoagulant composition; and
   a thixotropic gel;
   wherein, when the separator tube is at least partially filled with the whole blood and centrifuged at a force of about 1,500 g up to about 2,000 g for about 3 to about 10 minutes once in a single centrifugation, blood components in the whole blood are separated into at least: (i) the cosmetic or skin repair platelet concentrate containing greater than about 400 billion platelets per liter; and (ii) red blood cells.

27. The separator tube according to claim 1, wherein the therapeutic platelet concentrate contains less than about $0.6 \times 10^{12}$ red blood cells per liter.

28. The method according to claim 10, wherein the therapeutic platelet concentrate contains less than about $0.6 \times 10^{12}$ red blood cells per liter.

29. The separator tube according to claim 26, wherein the therapeutic platelet concentrate contains less than about $0.6 \times 10^{12}$ red blood cells per liter.

30. The separator tube according to claim 1, wherein the thixotropic gel is water insoluble and chemically inert to blood constituents.

31. The method according to claim 10, wherein the thixotropic gel is water insoluble and chemically inert to blood constituents.

32. The separator tube according to claim 26, wherein the thixotropic gel is non-toxic and non-mutagenic.

\* \* \* \* \*